US007622475B2

(12) United States Patent
Prasanna et al.

(10) Patent No.: US 7,622,475 B2
(45) Date of Patent: Nov. 24, 2009

(54) EP2 AGONISTS

(75) Inventors: Ganesh Prasanna, San Diego, CA (US); Charles Floyd Bosworth, Oceanside, CA (US); Jennifer Anne Lafontaine, San Diego, CA (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/829,176

(22) Filed: Jul. 27, 2007

(65) Prior Publication Data

US 2008/0045545 A1 Feb. 21, 2008

Related U.S. Application Data

(60) Provisional application No. 60/833,907, filed on Jul. 28, 2006, provisional application No. 60/941,923, filed on Jun. 4, 2007.

(51) Int. Cl.
*A01N 43/40* (2006.01)
*A61K 31/435* (2006.01)
*C07D 213/04* (2006.01)
*C07D 271/00* (2006.01)

(52) U.S. Cl. .................. 514/277; 546/255; 548/125
(58) Field of Classification Search ................ 546/255; 514/277; 548/125
See application file for complete search history.

(56) References Cited

U.S. PATENT DOCUMENTS

| 4,599,353 | A | 7/1986 | Bito |
| 5,296,504 | A | 3/1994 | Stjernschantz et al. |
| 6,288,120 | B1 | 9/2001 | Cameron et al. |
| 6,344,485 | B1 | 2/2002 | Cameron et al. |
| 6,492,412 | B2 | 12/2002 | Cameron et al. |
| 6,498,172 | B1 | 12/2002 | Cameron et al. |
| 6,649,657 | B2 | 11/2003 | Cameron et al. |
| 2002/0115695 | A1 | 8/2002 | Paralkar |
| 2002/0161026 | A1 | 10/2002 | Paralkar |
| 2003/0166631 | A1 | 9/2003 | Dumont et al. |
| 2004/0176423 | A1 | 9/2004 | Paralkar |
| 2005/0203086 | A1 | 9/2005 | Constan et al. |

FOREIGN PATENT DOCUMENTS

| EP | 1 000 619(A2) | 5/2000 |
| EP | 1 108 426(A2) | 6/2001 |
| EP | 1 205 189(A2) | 5/2002 |
| EP | 1 108 426(A3) | 10/2002 |
| WO | WO 98/28264 | 7/1998 |
| WO | WO 99/19300 | 4/1999 |
| WO | WO 9919300 | * 4/1999 |
| WO | WO 03/045371(A1) | 6/2003 |
| WO | WO 2004/078169 | 9/2004 |

OTHER PUBLICATIONS

Vippagunta et al., "Crystalline solids", Adv. Drug Delivery Reviews 48 (2001) 3-26.*
Anand, B.S., et al., "Current Prodrug Strategies Via Membrane Transporters/Receptors," *Expert Opinion on Biological Therapy*, 2002, 607-20, vol. 2, No. 6.
Beaumont, K., et al., "Design Of Ester Prodrugs To Enhance Oral Absorption of Poorly Permeable Compounds: Challenges To The Discovery Scientist," *Current Drug Metabolism*, 2003, 461-85, vol. 4, No. 6.
Ettmayer, G.L., et al., "Lessons Learned From Marketed And Investigational Prodrugs," *J. Med. Chem.*, 2004, 2393-2404, vol. 47, No. 10.
Flatch, A., et al., "Topical Prostaglandin $E_2$ Effects on Normal Human Intraocular Pressure", *Journal of Ocular Pharmacology*, 1988, 13-18, vol. 4, No. 1.
Papot, S., et al., "Design of Selectively Activated Anticancer Prodrugs: Elimination And Cyclization Strategies," *Current Medicinal Chemistry—Anti-Cancer Agents*, 2002, 155-85, vol. 2 No. 2.
Schultz, C., "Prodrugs of Biologically Active Phosphate Esters," *Bioorganic And Medicinal Chemistry*, 2003, 885-98, vol. 1, No. 6.
Smyth, T.P., et al., "Beta-Lactamase-Dependent Prodrugs—Recent Developments," *Tetrahedron*, 2000, 5699-5707, vol. 56, No. 31.
Stella, V. J., "Prodrugs As Therapeutics, Expert Opinion On Therapeutic Patents," 2004, 277-280, vol. 14, No. 3.
Testa, B., "Prodrug Research: Futile or Fertile?," *Biochemical Pharmacology*, 2004, 2097-2106, vol. 68, No. 11.
Testa, B., et al., "Design Of Intramolecularly Activated Prodrugs," *Drug Metabolism Review*, 1998, 787-807, vol. 30, No. 4.
Tsvetkova, B.P., et al., "Prodrugs And Hydrolysis Of Esters," *Pharmacia*, 2001, 45-57, vol. 48 Nos. 1-4.
Woodward, D.F., et al., "Molecular Characterization and Ocular Hypotensive Properties of the Prostanoid $EP_2$ Receptor," *Journal of Ocular Pharmacology and Therapeutics*, 1995, 447-454, vol. 11, No. 3.

\* cited by examiner

*Primary Examiner*—James O. Wilson
*Assistant Examiner*—Paul V. Ward
(74) *Attorney, Agent, or Firm*—Keith D. Hutchinson; Bryan C. Zielinski

(57) ABSTRACT

The invention provides EP2 agonists, methods for their preparation, pharmaceutical compositions containing these compounds, and methods of using these compounds and compositions for lowering intraocular pressure and thereby treating glaucoma.

7 Claims, 1 Drawing Sheet

US 7,622,475 B2

EP2 AGONISTS

This application claims the benefit of U.S. Provisional Application No. 60/833,907 filed Jul. 28, 2006, and U.S. Provisional Application No. 60/941,923 filed Jun. 4, 2007, the contents of which are hereby incorporated by reference in their entireties.

FIELD OF INVENTION

The invention relates to esters of EP2 agonists, methods for their preparation, pharmaceutical compositions containing these compounds, and methods of using these compounds and compositions for lowering intraocular pressure and thereby treating glaucoma.

BACKGROUND OF INVENTION

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye. The causes of aqueous humor accumulation in the anterior chamber are not fully understood. It is known that elevated intraocular pressure can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics. Latanoprost, a novel prostaglandin $F_2\alpha$ analogue, is a selective prostanoid FP receptor agonist which reduces the intraocular pressure by increasing the outflow of aqueous humor.

The relationship between EP receptor activation and intraocular pressure lowering effects is well known. There are currently four recognized subtypes of the EP receptor: EP1, EP2, EP3, and EP4 (J. Lipid Mediators Cell Signaling, volume 14, pages 83-87 (1996)). Intraocular pressure may be lowered by ligands capable of EP2 receptor activation, such as PGE2 and certain of its synthetic analogs (Journal of Ocular Pharmacology, volume 4, number 1, pages 13-18 (1988); Journal of Ocular Pharmacology and Therapeutics, volume 11, number 3, pages 447-454 (1995)).

Numerous publications have suggested the use of prostaglandin agonists for treating bone disorders and/or glaucoma, including: U.S. Pat. No. 4,599,353, U.S. Pat. No. 5,296,504, WO 1998/028264, U.S. Pat. No. 6,288,120, U.S. Pat. No. 6,492,412, U.S. Pat. No. 6,649,657, JP 2000053566, EP 1 000 619, U.S. Pat. No. 6,344,485, EP 1 205 189, US 2002/0115695, US 2002/0161026, US 2004/0176423, WO 2003/045371, US 2003/0166631, WO 1999/019300, U.S. Pat. No. 6,498,172, JP 20011163779, EP 1 108 426, US 2005/203086 and WO 2004/078169, the disclosures of each are hereby incorporated by reference in their entirety for all purposes. There remains, however, a continuing need in this field of art for alternative therapies for the treatment of glaucoma.

SUMMARY OF INVENTION

The invention is related to esters of EP2 agonists, pharmaceutical compositons thereof, and methods for reducing intraocular pressure in a mammal (including humans, male and/or female), comprising administering to a mammal a therapeutically effective amount of a compound selected from the group:

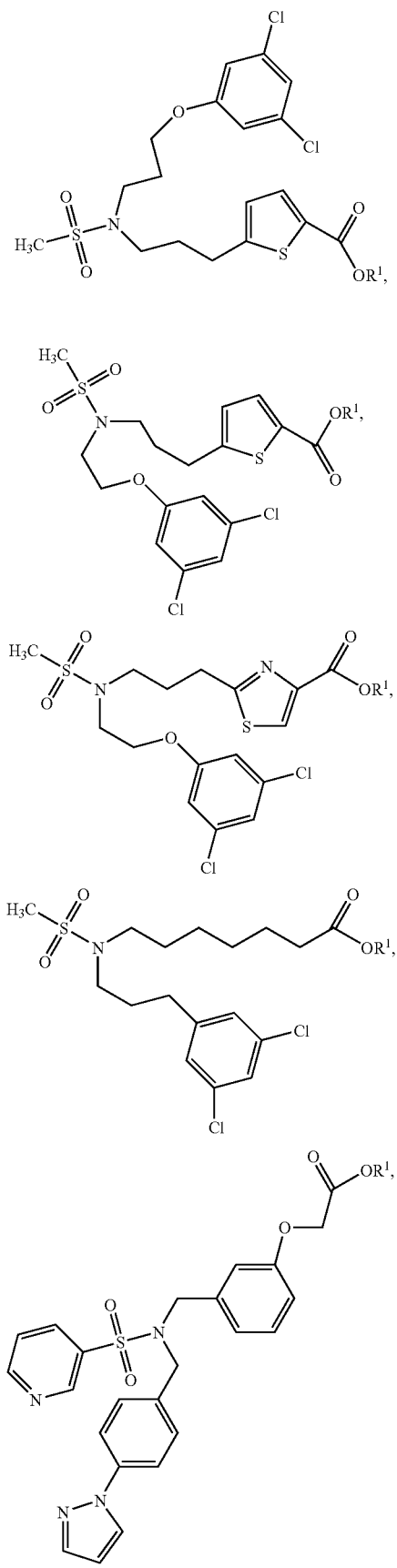

-continued
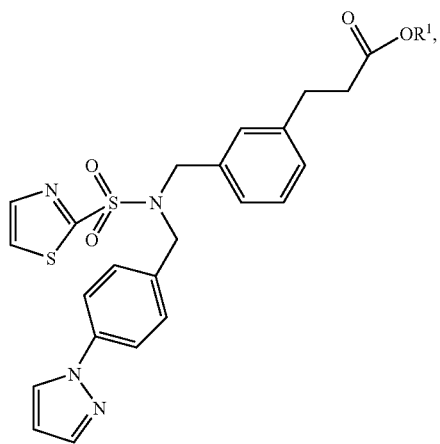
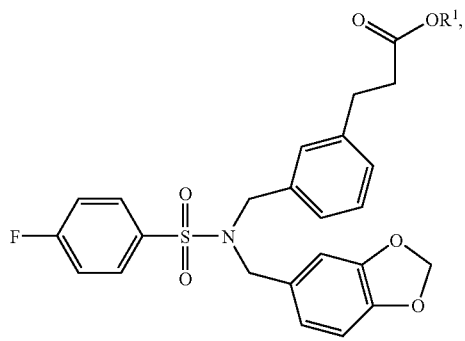
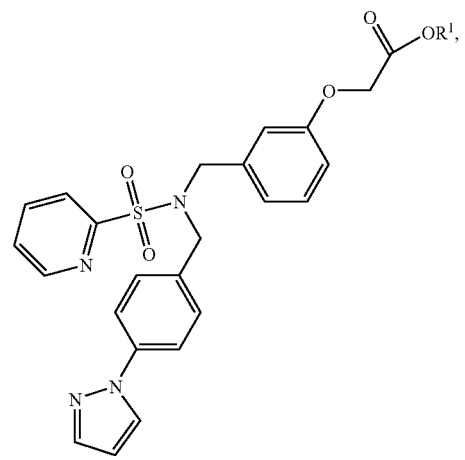
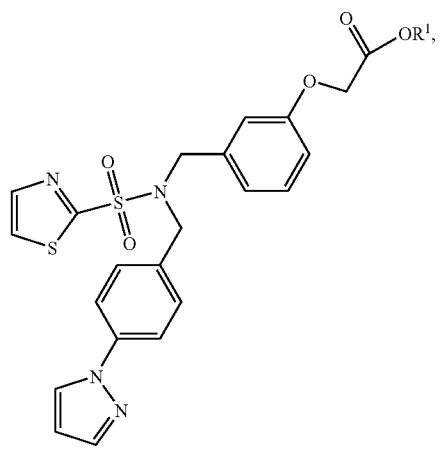
-continued
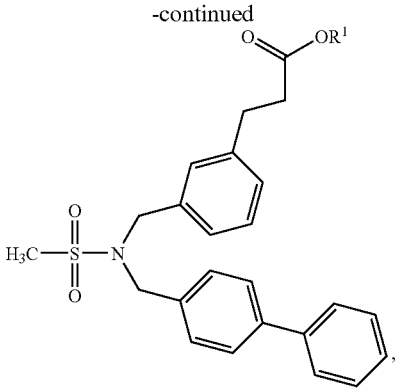
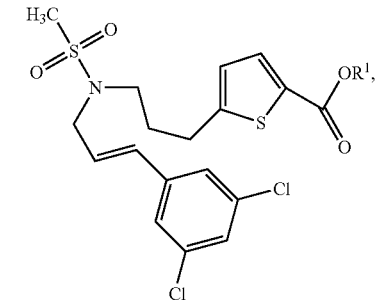
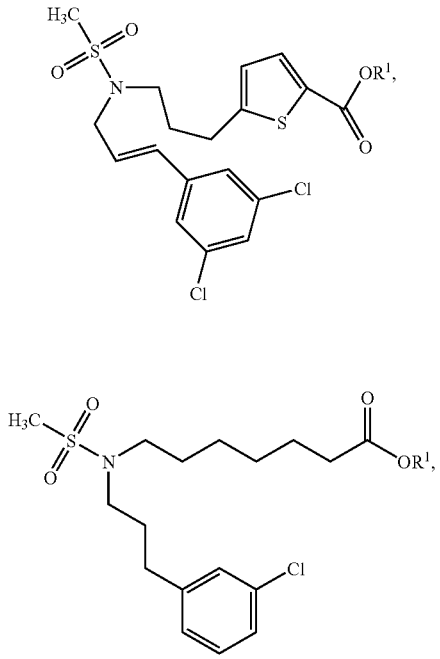
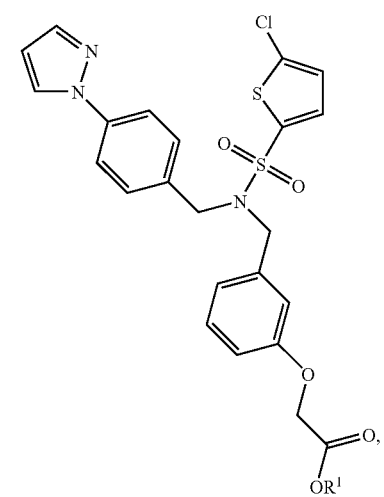

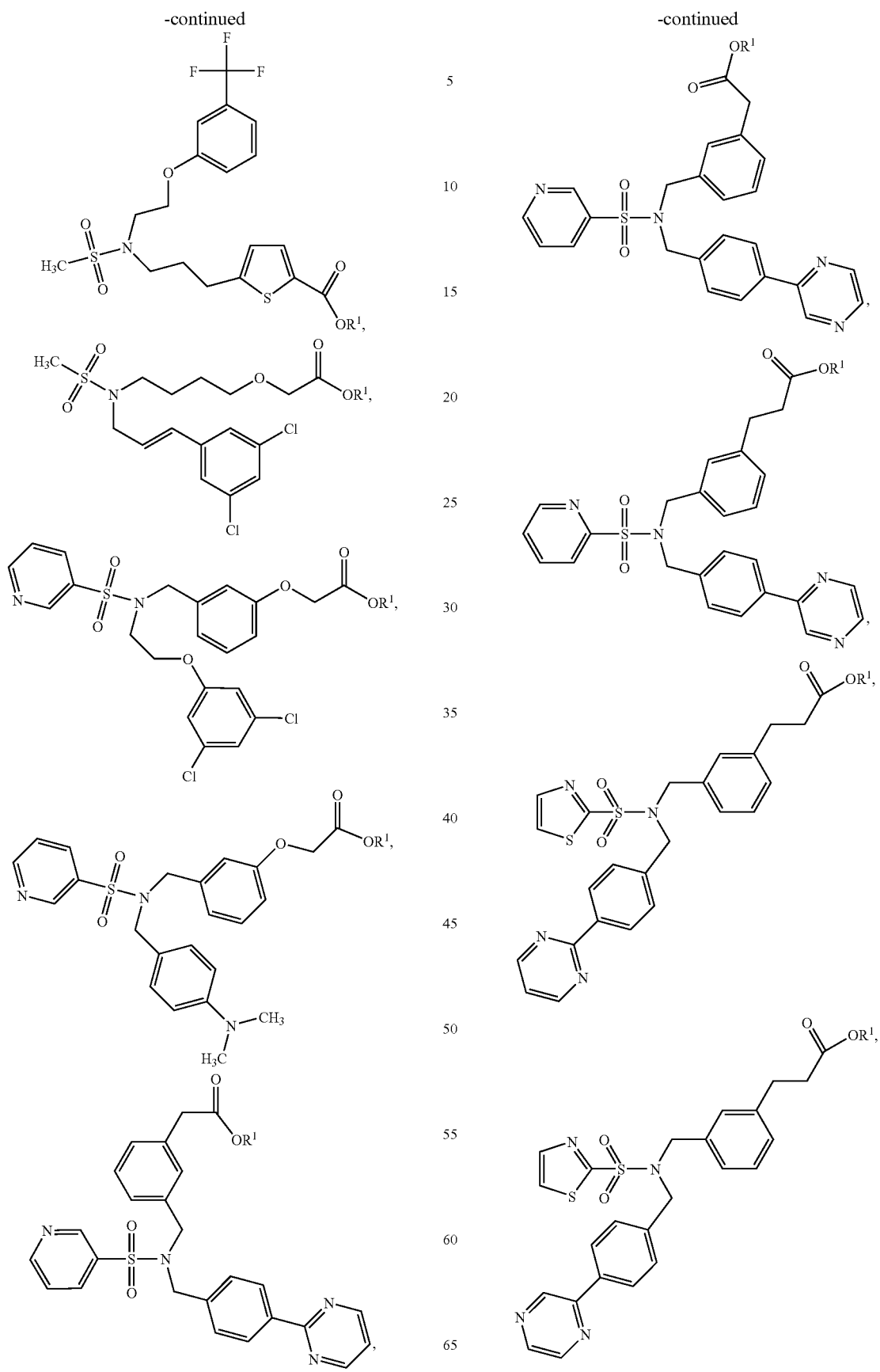

-continued
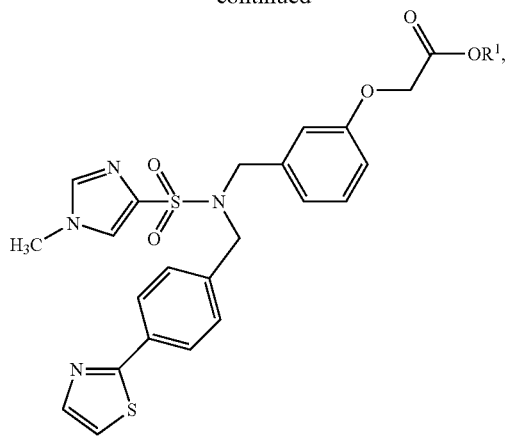
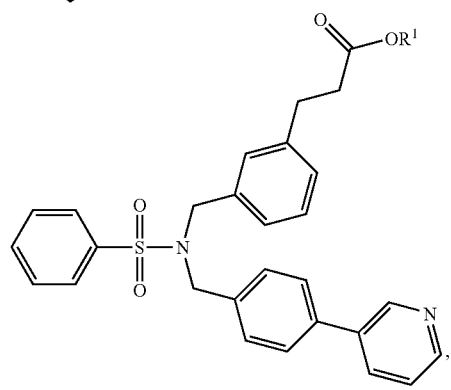
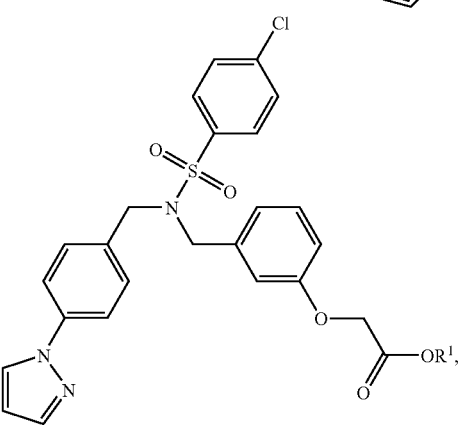
-continued
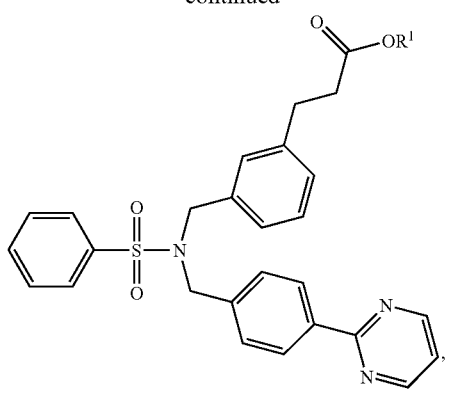
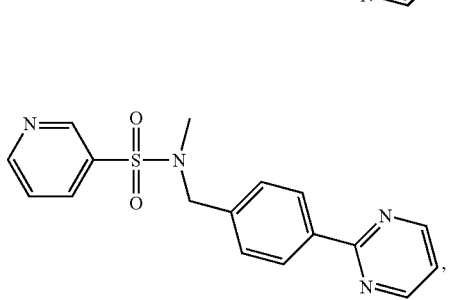

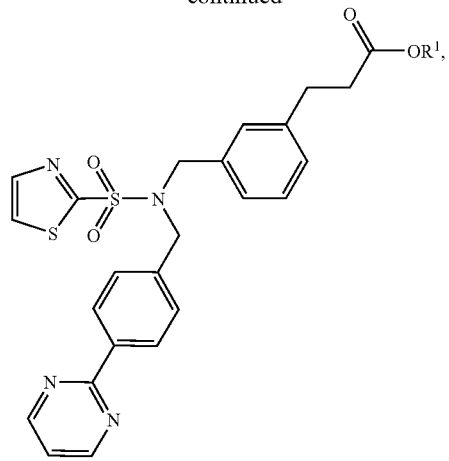
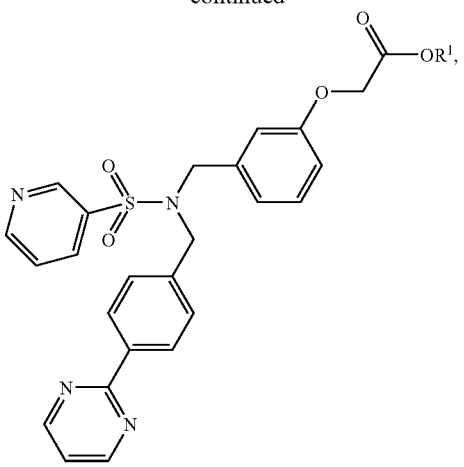
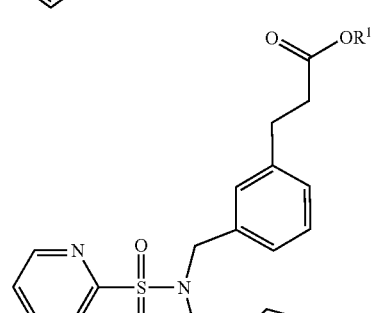
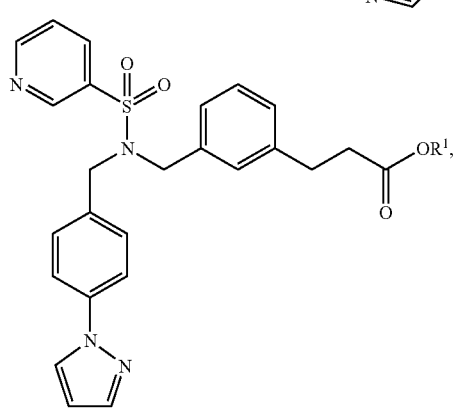

-continued
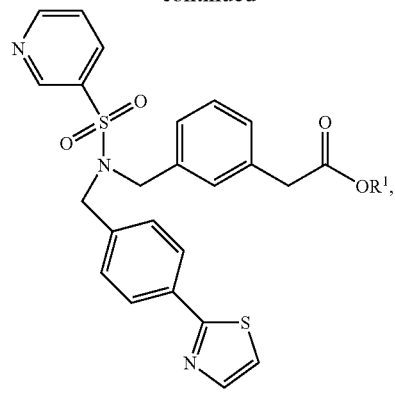
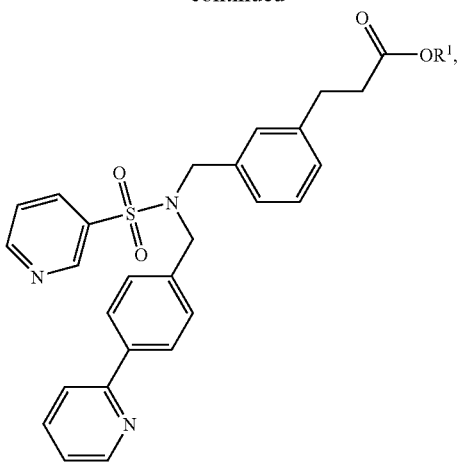
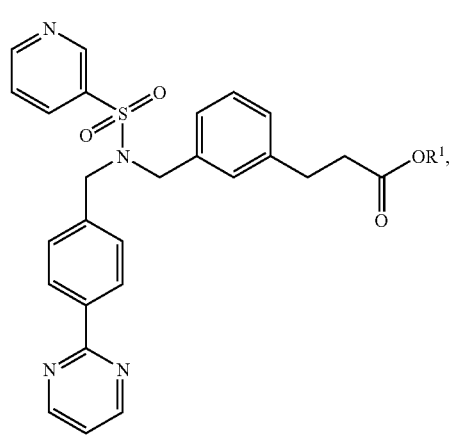
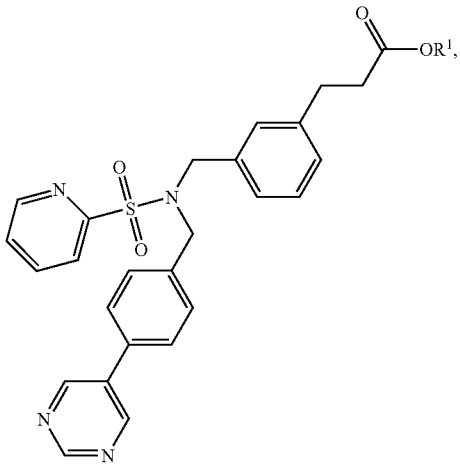
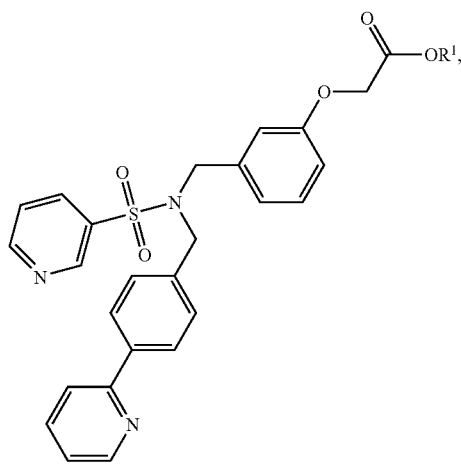
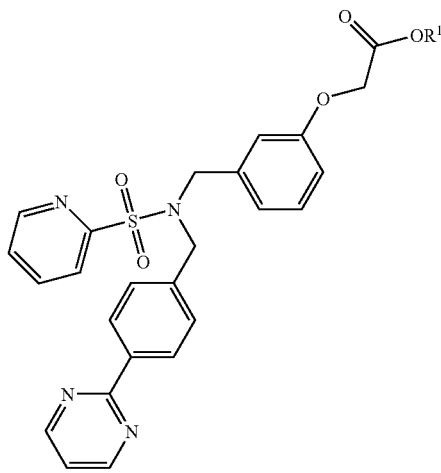
and -continued

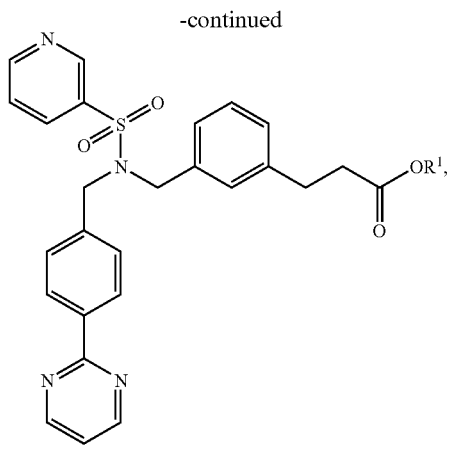

or a pharmaceutically acceptable salt or solvate thereof, wherein:

$R^1$ is $(C_1-C_{12})$alkyl, $(C_2-C_{12})$alkenyl, $(C_2-C_{12})$alkynyl, $(CR^2R^3)_b$—X—$(C_3-C_{12})$-alkyl, $(CR^2R^3)_b$—X-cyclo$(C_3-C_{12})$alkyl, $(CR^2R^3)_b$—X-cyclo$(C_2-C_{12})$alkenyl, $(CR^2R^3)_b$—X—$(C_6-C_{12})$aryl or $(CR^2R^3)_b$—X-(3-10)membered heterocyclyl, with the proviso that $R^1$ is not tert-butyl, and wherein $R^1$ is optionally substituted with 1 to 3 $R^5$ groups;

X is a bond, O, —S— or —$NR^4$;

$R^2$, $R^3$ and $R^4$ are each independently H or $(C_1-C_6)$alkyl;

each $R^5$ is independently —CN, —OH, —F, —Cl, —Br, —I, —$NO_2$, —$CF_3$, —$CHF_2$, —$CH_2F$, —$OCF_3$, —$N_3$, $(C_1-C_6)$alkoxy, $(C_1-C_6)$alkyl, $(C_2-C_6)$alkenyl, $(C_2-C_6)$alkynyl, —(C=O)$R^6$, —(C=O)$OR^6$, —O(C=O)$R^7$, —O(C=O)$NR^7$, —$NR^8$(C=O)$R^9$, —(C=O)$NR^8R^9$, —$NR^8R^9$, —$NR^8OR^9$, —S(O)$_j$$NR^8R^9$, —S(O)$_j$$(C_1-C_6)$alkyl, —OS(O)$_j$$R^9$, —$NR^8$S(O)$_j$$R^9$, —$(CR^{10}R^{11})_k(C_6-C_{12}$ aryl), —$(CR^{10}R^{11})_k$(3-10)-heterocyclyl, —$(CR^{10}R^{11})_k$(C=O)$(CR^{10}R^{11})_q(C_6-C_{12})$aryl, —$(CR^{10}R^{11})_k$(C=O)—$(CR^{10}R^{11})_q$-(3-10)-membered heterocyclyl, —$(CR^{10}R^{11})_k$O$(CR^{10}OR^{11})_q(C_6-C_{12})$aryl, —$(CR^{10}R^{11})_k$O—$(CR^{10}OR^{11})_q$(3-10) membered heterocyclyl, —$(CR^{10}OR^{11})_k$S(O)$_j$$(CR^{10}R^{11})_q(C_6-C_{12})$aryl or —$(CR^{10}R^{11})_k$S(O)$_j$$(CR^{10}R^{11})_q$(3-10) membered heterocyclyl;

any $(C_1-C_6)$alkyl, $(C_6-C_{12})$aryl and (3-10)membered heterocyclyl of the foregoing $R^5$ groups are each optionally independently substituted with 1 to 3 substituents, each independently selected from —CN, —F, —Cl, —Br, —I, —$NO_2$, —$CF_3$, —$CHF_2$, —$CH_2F$, —$OCF_3$, —$N_3$, —$OR^{12}$, —(C=O)$R^{12}$, —(C=O)$OR^{13}$, —O(C=O)$R^{13}$, —$NR^{13}$(C=O)$R^{14}$—(C=O)$NR^{15}R^{16}$, —$NR^{17}R^{18}$, —$NR^{14}OR^{15}$, $(C_1-C_6)$alkyl, $(C_2-C_6)$alkyl, $(C_2-C_6)$alkenyl, $(C_2-C_6)$alkynyl, —$(CR^{16}R^{17})_u(C_6-C_{12})$aryl and —$(CR^{16}R^{17})_v$(3-10)membered heterocyclyl;

$R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are each independently H, $(C_1-C_6)$alkyl, —(C=O)$N(C_1-C_6)$alkyl, —$(CR^{19}R^{20})_v(C_6-C_{12})$aryl or —$(CR^{19}R^{20})_v$(3-10) membered heterocyclyl;

any $(C_1-C_6)$alkyl, $(C_6-C_{12})$aryl and (3-10)membered heterocyclyl of the foregoing $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ groups are each optionally independently substituted with 1 to 3 substituents, each independently selected from —CN, —OH, —F, —Cl, —Br, —I, —$NO_2$, —$NR^{21}R^{22}$, —$CF_3$, —$CHF_2$, —$CH_2F$, —$OCF_3$, $(C_1-C_6)$alkyl, $(C_2-C_6)$alkenyl, $(C_2-C_6)$alkynyl and $(C_1-C_6)$alkoxy;

$R^{19}$, $R^{20}$, $R^{21}$ and $R^{22}$ are each independently H or $(C_1-C_6)$alkyl;

any 1 or 2 carbon atoms of the (3-10)membered heterocyclyl of each of the $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ and R groups are optionally substituted with oxo (=O);

and wherein any of the above-mentioned substituents comprising a —$CH_3$ (methyl), —$CH_2$ (methylene) or —CH (methine) group which is not attached to an —F. —Cl, —Br, —I, —SO or —$SO_2$ group or to a N, O or S atom, are optionally independently substituted with —OH, —F, —Cl, —Br, —I, $(C_1-C_6)$alkyl, $(C_1-C_6)$alkoxy, —$NH_2$, —$NH(C_1-C_6)$alkyl or —$N((C_1-C_6)$alkyl)$_2$;

j is 0, 1 or 2; and b, k, q, u and v are each independently 0, 1, 2, 3, 4, 5 or 6.

In another aspect, the invention relates to compounds, wherein $R^1$ is $(C_1-C_{12})$alkyl.

In another aspect, the invention relates to compounds, wherein $R^1$ is $(C_1-C_6)$alkyl.

In another aspect, the invention relates to compounds, wherein $R^1$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$ or —$CH_2CH(CH_3)CH_3$, In another aspect, the invention relates to compounds, wherein $R^1$ is —$CH_2CH_2OCH_3$, —$CH_2CH_2OCH_2CH_2OCH_3$, —$CH(CH_3)CH_2OH$ or —$CH(CH_3)CH_2OCH_3$.

In another aspect, the invention relates to compounds, wherein $R^1$ is —$CH(CH_3)_2$.

In another aspect, the invention relates to the compound:

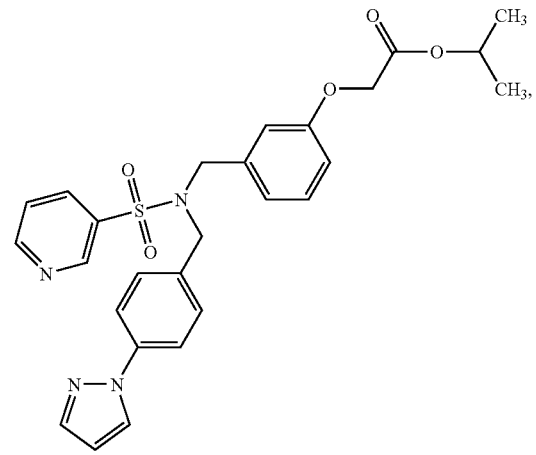

or a pharmaceutically acceptable salt or solvate thereof.

In another aspect, the invention relates to pharmaceutical compositions containing a compound of the invention, or pharmaceutically acceptable salts or solvates thereof, and a pharmaceutically acceptable excipient.

In another aspect, the invention relates to methods for reducing intraocular pressure in a mammal comprising administering to said mammal a therapeutically effective amount of a compound of the invention, or a pharmaceutically acceptable salt or solvate thereof.

In another aspect, the invention relates to methods for reducing intraocular pressure in a mammal, wherein the intraocular pressure is reduced in a human.

In another aspect, the invention relates to methods for reducing intraocular pressure in a mammal, wherein the intraocular pressure is reduced in treating glaucoma.

In another aspect, the invention relates to methods for reducing intraocular pressure in a mammal, wherein about 0.00001 mg/day to about 10 mg/day of a compound of the invention is administered.

In another aspect, the invention relates to methods for reducing intraocular pressure in a mammal, wherein about 0.005 mg/day of a compound of the invention is administered.

In another aspect, the invention relates to methods for reducing intraocular pressure in a mammal, wherein a compound of the invention is administered topically.

In another aspect, the invention relates to methods for reducing intraocular pressure in a mammal comprising administering to said mammal a therapeutically effective amount of a compound of formula:

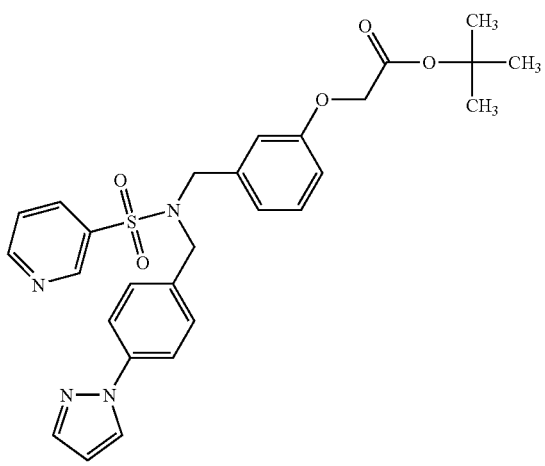

or a pharmaceutically acceptable salt or solvate thereof.

In another aspect, the invention relates to methods for reducing intraocular pressure in a mammal comprising administering to said mammal a therapeutically effective amount of a compound of the invention, or a pharmaceutically acceptable salt or solvate thereof.

In another aspect, the invention relates to methods for reducing intraocular pressure in a mammal, wherein glaucoma is treated in a human. In another aspect, the invention relates to methods for reducing intraocular pressure in a mammal, wherein about 0.00001 mg/day to about 10 mg/day of a compound of the invention is administered. In another aspect, the invention relates to methods for reducing intraocular pressure in a mammal, wherein a compound of the invention is administered topically.

In another aspect, the invention relates to methods for promoting neuroprotection. In yet another aspect, the invention relates to methods for preventing scar formation after glaucoma filtration surgery.

As used herein, the term "prodrug" refers to compounds that are drug precursors which following administration, release the drug in vivo via some chemical or physiological process (e.g., a prodrug on being brought to the physiological pH or through enzyme action is converted to the desired drug form). Prodrug strategies enhance the properties of a drug allowing it to overcome the inherent deficiencies in the pharmacokinetic properties of a drug. Prodrugs can also be used in certain circumstances to enhance the utility of a drug. Prodrugs differ from formulations in that chemical modifications lead to an entirely new chemical entity which upon administration to a patient regenerates the parent molecule within the body. A myriad of prodrug strategies exist which provide choices in modulating the conditions for regeneration of the parent drug. A number of reviews or discussions on prodrug strategies have been published and a nonexhaustive list is provided below, each of which is hereby incorporated by reference in their entirety: Prodrug Research: Futile Or Fertile?, Biochemical Pharmacology 68(11) pp 2097-2106; 2004 B. Testa; Prodrugs As Therapeutics, Expert Opinion On Therapeutic Patents, 14(3) pp 277-280; 2004, V. J. Stella; Lessons Learned From Marketed And Investigational Prodrugs, J. Med. Chem. 47(10), pp 2393-2404; 2004 P. Ettmayer, G. L. Amidon, B. Clement and B. Testa; Prodrugs of Biologically Active Phosphate Esters, Bioorganic And Medicinal Chemistry 11(6), pp 885-98; 2003, C. Schultz; Design Of Ester Prodrugs To Enhance Oral Absorption of Poorly Permeable Compounds: Challenges To The Discovery Scientist, Current Drug Metabolism 4(6) pp 461-85; 2003, K. Beaumont, R. Webster, I. Gardner and K. Dack; Design Of Selectively Activated Anticancer Prodrugs: Elimination And Cyclization Strategies, Current Medicinal Chemistry—Anti-Cancer Agents, 2(2) pp 155-85; 2002, S. Papot, I. Tranoy, F. Tillequin, J. C. Florent and J. P. Gesson, UMR 6514, Faculte des Sciences, 40 avenue du recteur Pineau, 86022 Poitiers, France; Current Prodrug Strategies Via Membrane Transporters/Receptors, Expert Opinion on Biological Therapy 2(6) pp 607-20; 2002, B. S. Anand, S. Dey and A. K. Mitra, Division of Pharmaceutical Sciences, School of Pharmacy, University of Missouri-Kansas City, 5005 Rockhill Road, Kansas City, Mo. 64110-2499, USA; Prodrugs And Hydrolysis Of Esters, Pharmacia 48(1-4) pp 45-57; 2001, B. Tsvetkova, P. Peikov and J. Tencheva; Beta-Lactamase-Dependent Prodrugs—Recent Developments, Tetrahedron 56(31) pp 5699-5707; 2000, T. P. Smyth, M. E. O'Donnell, M. J. O'Connor and J. O. St Ledger; Design Of Intramolecularly Activated Prodrugs, Drug Metabolism Reviews 30(4) pp 787-807; 1998, B. Testa and J. M. Mayer, School of Pharmacy, University of Lausanne, Switzerland; and Hydrolysis in Drug and Prodrug Metabolism, Chemistry, Biochemistry, and Enzymology. Richard Testa, Joachim Mayer, 2003 Wiley-VCH publisher, ISBN 3-906390-25-X.

A major aim of prodrug design is to improve the pharmacokinetic behaviour of active carboxylic acids. A carboxylic acid group, being ionized in the physiological pH range, contributes significantly to reducing the lipophilicity of compounds containing this moiety. As a result, a large number of pharmacologically active carboxylic acids display unfavourable pharmacokinetic properties such as low bioavailabilty, a problem of particular concern for compounds that contain other moieties of high polarity.

The compounds of the invention may be administered as prodrugs. Certain derivatives of the compounds of the invention may have little or no pharmacological activity themselves can, when administered into or onto the body, be converted into compounds having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and Bioreversible Carriers in Drug Design', Pergamon Press, 1987 (ed. E B Roche, American Pharmaceutical Association).

Prodrugs can, for example, be produced by replacing appropriate functionalities present in the compounds of the invention with certain moieties known to those skilled in the art as 'pro-moieties' as described, for example, in "Design of Prodrugs" by H Bundgaard (Elsevier, 1985). Some examples of such prodrugs include where the compounds of the invention contains a carboxylic acid functionality (—COOH), an ester thereof, for example, replacement of the hydrogen with ($C_1$-$C_{20}$)alkyl, ($C_1$-$C_{12}$)alkyl, ($C_1$-$C_6$)alkyl or ($C_1$-$C_3$)alkyl. Further examples of replacement groups in accordance with the foregoing examples and examples of other prodrug types may be found in the aforementioned references.

Exemplary prodrugs upon cleavage release the corresponding free acid and such hydrolyzable ester compounds include but are not limited to substituents wherein the carboxyl free hydrogen is replaced by ($C_1$-$C_{20}$)alkyl, ($C_1$-$C_{12}$)alkyl, ($C_2$-$C_7$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton4-yl, di-N,N—($C_1$-$C_2$)alkylamino($C_2$-$C_3$)alkyl (such as b-dimethylaminoethyl), carbamoyl-($C_1$-$C_2$)alkyl, N,N-di($C_1$-$C_2$)alkylcarbamoyl-($C_1$-$C_1$)alkyl and piperidino-, pyrrolidino- or morpholino($C_2$-$C_3$)alkyl.

Hydrolyzable ester forming residues upon cleavage release the corresponding carboxylic acid. Such prodrugs include but are not limited to those having substituents wherein the carboxylic acid hydroxyl hydrogen is replaced by an alkyl, alkenyl or alkynyl group. These groups may be straight or branched chains and may form cyclic structures such as cycloalkyl, cycloalkenyl and cycloalkynyl moieties and also include bridged structures such as norbornyl and adamantyl groups. Exemplary alkyl groups include but are not limited to methyl, ethyl, n-propyl, iso-propyl, n-butyl, sec-butyl, tert-butyl, and the like. More complex alkyl groups include more lipophillic terpenoid derivatives such as limonenyl, perillyl, bornyl and menthyl esters.

Other prodrug carboxylic acid ester substituents involve alkoxy derivatives including but not limited to alkoxyalkyl, alkoxyalkenyl, alkoxyalkynyl, alkoxycycloalkyl, alkoxycycloalkenyl, alkoxycycloalkynyl, alkoxyalkylcycloalkyl, alkoxyalkylcycloalkenyl, alkoxyalkylcycloalkynyl, alkoxyalkenylcycloalkyl, alkoxyalkenylcycloalkenyl, alkoxyalkenylcycloalkynyl, alkoxyalkynylcycloalkyl, alkoxyalkynylcycloalkenyl and alkoxyalkynylcycloalkynyl groups.

Other prodrug carboxylic acid ester substituents involve aryl derivatives including but not limited to phenyl, naphthyl, indenyl, azulenyl, fluorenyl and anthracenyl groups. Also included are alkylaryl, alkenylaryl, alkynylaryl, alkoxyaryl, alkoxyalkylaryl, alkoxyalkenylaryl and alkoxyalkynylaryl groups.

Other prodrug carboxylic acid ester substituents involve heterocyclic derivatives including but not limited to furyl, thiophenyl, pyrrolyl, pyrrolinyl, pyrrolidinyl, dioxolanyl, oxazolyl, thiazolyl, indazolyl, imidazolyl, inidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, dithianyl, thiomorpholinyl, pyridazinyl, pyrimidinyl, pyrazinyl, piperazinyl, triazinyl, trithianyl, indolizinyl, indolyl, isoindolyl, indolyl, indolinyl, benzo[b]furyl, benzo[b]thiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthridinyl, pteridinyl, quinuclidinyl, carbazolyl, acridinyl, phenazinyl, phenothiazinyl, phenoxazinyl, indenyl, naphthalenyl, azulenyl, fluorenyl, anthracenyl, norbornanyl and adamantanyl groups. Also included are alkyl-heterocyclic, alkenylheterocyclic, alkynyl heterocyclic, alkoxyheterocyclic, alkoxyalkyl-heterocyclic, alkoxyalkenylheterocyclic and alkoxyalkynylheterocyclic groups. The corresponding partially and fully saturated moieties for these groups are also included, e.g., alkyltetrahydrofuran and alkyltetrahydropyran groups.

Other prodrug carboxylic acid ester substituents involve carbamolylmethyl esters, i.e., —$CH_2CO$—NRR groups including but not limited to groups where R and R are each independently substituted with H, alkyl, alkylamino, alkoxyalkyl, acetamidyl, alkylcarbonic acid alkyl ester or R and R form 4, 5 or 6 membered cyclic or heterocyclic structures such as morpholinyl or piperidinyl groups.

Other prodrug carboxylic acid ester substituents involve aminoalkyl groups and alkylheterocyclic groups containing one or more N atoms including but not limited to alkylpyrrolyl, alkylpyrrolinyl, alkylpyrrolidinyl, alkyloxazolyl, alkylthiazolyl, alkylimidazolyl, alkylimidazolinyl, alkylimidazolininyl, alkylpyrazolyl, alkylpyrazolinyl, alkylpyrazolininyl, alkylisoxazolyl, alkylisothiazolyl, alkyloxadiazolyl, alkyltriazolyl, alkylthiadiazolyl, alkyl pyridinyl, alkyl piperidinyl, alkylmorpholinyl, alkylthiomorpholinyl, alkylpyridazinyl, alkylpyrimidinyl, alkylpyrazinyl, alkylpiperazinyl, alkyltriazinyl, alkylindolizinyl, alkylindolyl, alkylisoindolyl, alkylindolyl, alkylindolinyl, alkylindazolyl, alkylbenzimidazolyl, alkylbenzthiazolyl, alkylpurinyl, alkylquinolizinyl, alkylquinolinyl, alkylisoquinolinyl, alkylcinnolinyl, alkylphthalazinyl, alkylquinazolinyl, alkylquinoxalinyl, alkylnaphthyridinyl, alkylpteridinyl, alkylquinuclininyl, alkylcarbazolyl, alkylacridinyl, alkylphenazinyl, alkylphenothiazinyl and alkylphenoxazinyl groups.

Still other prodrug carboxylic acid ester substituents involve triglycerides; glycolic acid esters; (acyloxy)alkyl esters; [(alkoxycarbonyl)oxy]methyl esters; amidomethyl esters; alkylamino esters; oxodioxolyl)methyl esters; and N,N-dialkylhydroxylamino esters.

Activation of the inducible isoform of cyclooxygenase, COX-2, is neurotoxic in acute and chronic models of neurological disease (Dore S, Otsuka T, Mitro T, et al. Neuronal overexpression of cyclooxygenase-2 increases cerebral infarction. Ann Neurol. 2003; 54:155-162). While the exact mechanism by which COX-2 promotes neural degeneration is unknown it is presumed to involve the downstream regulation of prostaglandins and/or oxidative stress because cyclooxygenases catalyze the conversion of arachidonic acid to PGH2. PGH2 is converted by prostaglandin synthases into PGE2, PGF2α, PGD2, PGI2, and TxA2 (Liu D, Wu L, Breyer R, Mattison M P, Anddreasson K. Neuroprotection by the PGE2 EP2 receptor in permanent focal cerebral ischemia. Ann Neurol. 2005; 57:758-761). Of these, PGE2 is a proinflammatory prostaglandin which is tightly coupled to COX-2 activation. PGE2 binds to four G-protein-coupled receptors (EP1, EP2, EP3, and EP4). Of these, activation of the EP2 receptor has been found to promote neuroprotection in excitotoxic motor neuron degeneration (Bilak M, Wu I, Wang Q, et al. PGE2 receptors rescue motor neurons in a model of amyotrophic lateral sclerosis. Ann Neurol. 2004; 56:240-248), NMDA toxicity and oxygen glucose deprivation (McCullough L, Wu L, Haughey N, et al. Neuroprotective function of the PGE2 EP2 receptor in cerebral ischemia. J Neuroscience. 2004; 24:257-268), and in amyloid-β (Yagami T, Nakazato H, Ueda K, et al. Prostaglandin E2 rescues cortical neurons from amyloid beta protein-induced apoptosis. Brain Res. 2003; 959: 328-335) and inflammatory neurotoxicity (Lee E O, Shin Y J, Chong Y H. Mechanisms involved in prostaglandin E2-mediated neuroprotection against TNF-alpha: possible involvement of multiple signal transduction and beta-cetenin/T-Cell factor. J Neuroimmunol. 2004; 155:21-31).

Studies involving young cynomologous monkeys subjected to topical ocular QD dosing with AH-13205 (EP2 agonist) for 1 year revealed that there was doubling in the number of nerve bundles in ciliary muscle not only in the treated eyes but also in the contralateral eyes. The increase in nerve bundles and the nerve sprouting were restricted to the longitudinal and reticular portions of the ciliary muscle and could possibly be attributed to enlargement of intermuscular spaces and/or stimulation of neurotrophic growth factors (Richter M, Krauss A H, Woodward D F, Lutjen-Drecoll E. Morphological changes in the anterior eye segment after long-term treatment with different receptor selective prostaglandin agonists and a prostamide. Invest Ophthalmol Vis Sci. 2003, 44(10):4419-26). In newborn piglets, exposure to brief hypoxia in the presence of PG synthase inhibitors and/or the EP2 agonist, butaprost resulted in restoration of electrophysiological changes (VEPs and ERGs) that were reduced with PG synthase inhibitors alone suggesting that EP2 receptor agonism may preserve neural function (Najarian T, Hardy P, Hou X, Lachapelle J, Doke A, Gobeil F Jr, Roy M S, Lachapelle P, Varma D R, Chemtob S. Preservation of neural function in the perinate by high PGE(2) levels acting via EP(2) receptors. J Appl Physiol. 2000 August; 89(2):777-84). PGE2 has been shown to stimulate synthesis and secretion of brain-derived neurotrophic factor (BDNF) and nerve growth factor (NGF) from murine astrocyte cultures, also indicative of PG-induced neuroprotection (Toyomoto M, Ohta M, Okumura K, Yano H, Matsumoto K, Inoue S, Hayashi K, Ikeda K. Prostaglandins are powerful inducers of NGF and BDNF production in mouse astrocyte cultures. FEBS Lett. 2004; 562(1-3):211-5).

The EP2 receptor has been identified in the plexiform and nerve fiber layers of the human retina and in the cornea, conjunctiva, sclera, and lens (Schlotzer-Schrehardt U, Zenkel M, Nusing R M. Expression and localization of FP and EP prostanoid receptor subtypes in human ocular tissues. Inves Ophthalmol Vis Sci. 2002; 43:1475-1487) suggesting that EP2 receptor agonists may be neuroprotective for both retinal neurodegenerative diseases (eg, Glaucoma, DME, and AMD) and diseases which affect the subbasel neural plexis of the cornea.

Consistent with a potential roll for an EP2 agonist in the treatment of dry eye is evidence suggesting that the disease may actually be a neurotrophic keratopathy characterized by the loss of subbasel afferents and/or parasympathetic neural transmission (Benitez del Castillo J M, Wasfy M A S, Fernandez C, Garcia-Sanchez J. An in vivo confocal masked study on corneal epithelium and subbasal nerves in patients with dry eye. Inves Ophthalmol Vis Sci. 2004; 45:3030-3035). This concept of dry eye emphasizes that the ocular surface (cornea, conjunctiva, accessory lacrimal glands, and meibomian glands), the main lacrimal gland, and reflexive innervation form a single functional unit. According to this theory, alteration of nerve stimulation to the main lacrimal gland will result in inflammation and lymphocytic infliltration (Stern M E, Beuerman R W, et al. A unified theory of the role of the ocular surface in dry eye. Lacrimal Gland, Tear Film, and Dry Eye Syndromes 2 edited by Sullivan et al, Plenum Press, New York, 1998). Inflammation and lymphocytic infiltration will subsequently result in the secretion of cytokines which can further impair parasympathetic neural transmission to the main lacrimal gland, the accessory glands, and the conjunctival goblet cells (Stern M E, Beuerman R W, et al. A unified theory of the role of the ocular surface in dry eye. Lacrimal Gland, Tear Film, and Dry Eye Syndromes 2 edited by Sullivan et al, Plenum Press, New York, 1998).[12] Thus, EP2 agonist by virtue of their ability to protect subbasel afferents and/or parasympathetic neural signaling in patients suffering from either non-Sjogren's related dry eye (ie, keratoconjunctivitis sicca) or Sjogren's related dry eye may represent a novel treatment option for dry eye.

Consistent with a duel mechanism of action for an EP2 receptor agonist in glaucoma, neuroprotection and IOP reduction, Choung and Colleagues (1998) have demonstrated that prostaglandin E2 (PGE2) ablates interleukin-1beta (IL-1beta) and transforming growth factor-beta (TGFbeta) lysyl oxidase (LO) mRNA levels (Choung J, Taylor L, Thomas K, Zhou X, Kagan H, Yang X, Polgar P.

In addition, an EP2 receptor agonist may have an opportunity to enhance long term treatment outcomes following glaucoma filtration surgery. Scar formation is a major source of failure for glaucoma filtration surgery. Limiting fibrotic response is important for limiting scar formation and tissue fibrosis. The deposition of collagen into extracellular connective tissue matrix requires the presence of lysyl oxidase (LO). Choung J, et al. Role of EP2 receptors and cAMP in prostaglandin E2 regulated expression of type I collagen alpha1, lysyl oxidase, and cyclooxygenase-1 genes in human embryo lung fibroblasts. J Cell Biochem. 1998; 71:254-63. E2 (PGE2) inhibits the expression of LO mRNA levels.

Role of EP2 receptors and cAMP in prostaglandin E2 regulated expression of type I collagen alpha1, lysyl oxidase, and cyclooxygenase-1 genes in human embryo lung fibroblasts. J Cell Biochem. 1998; 71:254-63). TGFbeta upregulates several extracellular matrix genes (eg, versican, elastin, collagens, fibrillin, laminin, and fibulin) possibly leading to increased outflow resistance in the trabecular meshwork. TGFbeta levels are elevated in glaucomatous eyes (Fleenor D L, Shepard A R, Hellberg P E, Jacobson N, Pang I, Clark A F. TGFb2-induced changes in human trabecular meshwork: implications for intraocular pressure. Inves Ophthalmol Vis Sci. 2006; 47:226-234). Thus, ablation of TGFbeta mRNA levels with an EP2 receptor agonist may increase traditional outflow and subsequently reduce IOP in glaucomatous eyes.

As used herein, the terms "comprising" and "including" are used in their open, non-limiting sense.

As used herein, the term "substituted," means that the specified group or moiety bears one or more substituents. The term "unsubstituted," means that the specified group bears no substituents.

As used herein, the term "optionally substituted" means that the specified group is unsubstituted or is substituted by one or more substituents.

As used herein, the terms "treat," "treating" or "treatment" includes preventative (e.g., prophylactic) and palliative treatment.

As used herein, the term "pharmaceutically acceptable" means the carrier, diluent, excipients and/or salt must be compatible with the other ingredients of the formulation and not deleterious to the recipient thereof.

As used herein, the term "alkyl" means a straight or branched chain saturated hydrocarbon. Exemplary alkyl groups include but are not limited to methyl, ethyl, propyl, isopropyl, n-butyl, sec-butyl, tert-butyl, pentyl, isopentyl, neopentyl, tert-pentyl, 1-methylbutyl, 2-methylbutyl, 3-methylbutyl, hexyl, isohexyl, heptyl, octyl and the like.

As used herein, the term "alkenyl" means a straight or branched chain hydrocarbon having at least one double bond, i.e., a C=C. Exemplary alkenyl groups include but are not limited to vinyl, propenyl, butenyl, pentenyl, hexenyl, heptenyl, octenyl and the like.

As used herein, the term "alkynyl" means a straight or branched chain hydrocarbon having at least one triple bond, i.e., a C≡C. Exemplary alkynyl groups include but are not limited to acetylenyl, propargyl, butynyl, pentynyl, hexynyl, heptynyl, octynyl and the like.

As used herein, the term "cycloalkyl" means a cyclic saturated hydrocarbon. Exemplary cycloalkyl groups include but are not limited to cyclopropyl, cyclobutyl, cyclopentyl, cyclohexyl, cycloheptyl, cyclooctyl and the like.

As used herein, the term "cycloalkenyl" means a cyclic hydrocarbon having at least one double bond, i.e., a C=C. Exemplary cycloalkenyl groups include but are not limited to cyclopropenyl, cyclobutenyl, cyclopentenyl, cyclohexenyl, cycloheptenyl, cyclooctenyl and the like.

As used herein, the term "cycloalkynyl" means a cyclic hydrocarbon having at least one triple bond, i.e., a C≡C. Exemplary cycloalkynyl groups include but are not limited to cyclohexynyl, cycloheptynyl, cyclooctynyl and the like.

As used herein, the term "alkoxy" means a straight or branched chain saturated alkyl group bonded through oxygen. Exemplary alkoxy groups include but are not limited to methoxy, ethoxy, propoxy, isopropoxy, butoxy, isobutoxy, tert-butoxy, pentoxy, isopentoxy, neopentoxy, tert-pentoxy, hexoxy, isohexoxy, heptoxy, octoxy and the like.

As used herein, the term "alkylene" means a straight chain or branched chain saturated hydrocarbon wherein a hydrogen atom is removed from each of the terminal carbons. Exemplary alkylene groups include but are not limited to methylene, ethylene, propylene, butylene, pentylene, hexylene, heptylene and the like.

As used herein, the term "halo" or "halogen" means chloro, bromo, iodo or fluoro.

As used herein, the term "aryl" means an organic radical derived from an aromatic hydrocarbon by removal of hydrogen. Exemplary aryl groups include but are not limited to phenyl, naphthyl and the like.

As used herein, the terms "heterocyclic" means an aromatic or non-aromatic cyclic group containing one to four heteroatoms each independently selected from O, S and N, wherein each group has from 3 to 10 atoms in its ring system. Non-aromatic heterocyclic groups include groups having only 3 atoms in their ring system, whereas aromatic heterocyclic groups have at least 5 atoms in their ring system. Heterocyclic groups include fused ring systems such as benzo-fused rings and the like. An exemplary 3 membered heterocyclic group is aziridine; 4 membered heterocyclic group is azetidinyl (derived from azetidine); 5 membered heterocyclic group is thiazolyl; 7 membered ring heterocyclic group is azepinyl; and a 10 membered heterocyclic group is quinolinyl. Examples of non-aromatic heterocyclic groups include but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic(heteroaryl) groups include but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Heterocyclic groups may be optionally substituted on any ring carbon, sulfur or nitrogen atom(s) by one to two oxygens (oxo), per ring. An example of a heterocyclic group wherein 2 ring carbon atoms are substituted with oxo moieties is 1,1-dioxo-thiomorpholinyl.

Examplary five to six membered heterocyclic aromatic rings having one or two heteroatoms selected independently from oxygen, nitrogen and sulfur include but are not limited to isothiazolyl, pyridinyl, pyridiazinyl, pyrimidinyl, pyrazinyl and the like.

Exemplary partially saturated, fully saturated or fully unsaturated five to eight membered heterocyclic rings having one to four heteroatoms selected independently from oxygen, sulfur and nitrogen include but are not limited to 3H-1,2-oxathiolyl, 1,2,3-oxadizaolyl, 1,2,4-oxadiazolyl, 1,2,5-oxadiazolyl and the like. Further exemplary five membered rings are furyl, thienyl, 2H-pyrrolyl, 3H-pyrroyl, pyrrolyl, 2-pyrrolinyl, 3-pyrrolinyl, pyrrolidinyl, 1,3-dioxolanyl, oxazolyl, thiazolyl, thiazolyl, imidazolyl, 2H-imidazolyl, 2-imidazolinyl, imidazolidinyl, pyrazolyl, 2-pyrazolinyl, pyrazolinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 1,2,3,4-oxatriazolyl, 1,2,3,5-oxatrizaolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl. Further exemplary six member rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-trizainyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings are azepinyl, oxepinyl, thiepinyl and 1,2,4-diazepinyl. Further exemplary eight membered rings are cyclooctyl, cyclooctenyl and cyclooctadienyl.

Exemplary bicyclic rings are composed of two fused partially saturated, fully saturated or fully unsaturated five or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4Hquinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

Pharmaceutically acceptable salts of the compounds of the invention include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of the invention may be readily prepared by mixing together solutions of a compound of the invention and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising a compound of the invention and one or more pharmaceutically acceptable solvent molecules, for example, ethanol, water and the like. The term 'hydrate' is included within the meaning of the term "solvate" and is frequently used when the solvent is water. Pharmaceutically acceptable solvates in accordance with the invention include solvates (hydrates) wherein the solvent of crystallization may be isotopically substituted, e.g. $D_2O$, $d_6$-acetone, $d_6$-DMSO.

The compounds of the invention which are complexes, such as clathrates and drug-host inclusion complexes are within the scope of the invention. In contrast to the aforementioned solvates, the drug and host are present in stoichiometric or non-stoichiometric amounts. Also included are complexes containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of the invention include all compounds of the invention, polymorphs and isomers thereof, including optical, geometric and tautomeric isomers as hereinafter defined and isotopically-labeled compounds.

The compounds of the invention containing one or more asymmetric carbon atoms may exist as two or more stereoisomers. Where a compound contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

All stereoisomers, geometric isomers and tautomeric forms of the compounds of the invention are included within the scope of the invention, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art [see, for example, "Stereochemistry of Organic Compounds" by E. L. Eliel (Wiley, New York, 1994)].

The invention includes all pharmaceutically acceptable isotopically-labelled compounds of the invention, wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$, and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

As used herein, the expressions "reaction-inert solvent" and "inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

One of ordinary skill will recognize that certain compounds of the invention may contain one or more atoms which may be in a particular stereochemical or geometric configuration, giving rise to stereoisomers and configurational isomers. All such isomers and mixtures thereof are included in the invention. Solvates (hydrates) of the compounds of the invention are also included.

Other features and advantages will be apparent from the specification and claims which describe the invention.

DETAILED DESCRIPTION OF INVENTION

Figure 1:
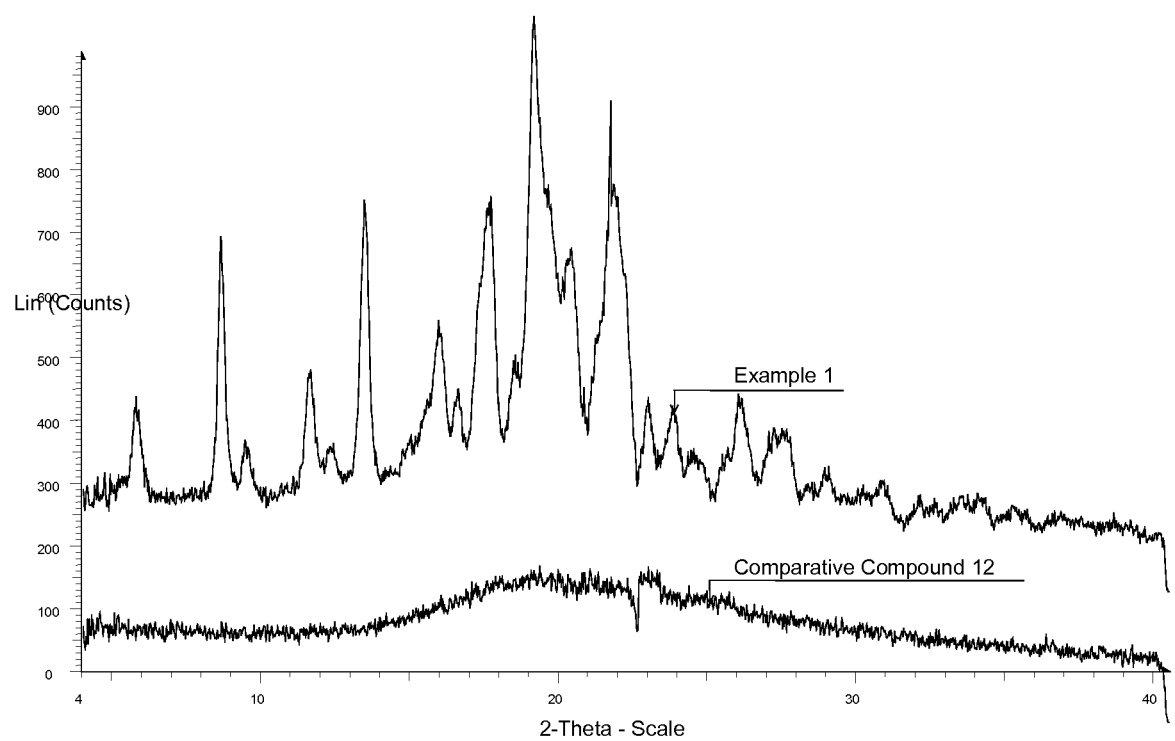
FIG. 1 is a powder X-ray diffraction diagram of Example 1, isopropyl [3-({[4-(1H-pyrazol-1-yl)benzyl](pyridin-3-yl-sulfonyl)amino}methyl)phenoxy]acetate, and the comparative compound 12 (C12), t-butyl [3-({[4-(1H-pyrazol-1-yl)benzyl](pyridin-3-yl-sulfonyl)amino}methyl)phenoxy]acetate.

The compounds of the invention may be prepared by processes known in the chemical arts, particularly in light of the description contained herein. Certain processes for the manufacture of the compounds of the invention are provided as further features of the invention and are illustrated by the following reaction schemes and examples.

The compounds of the invention may be prepared by any of the following routes: a) sequential alkylation of a sulphonamide with two appropriate alkylating agents, generally alkyl halides or alkyl sulfonates; b) alkylation of a sulphonamide with an alkyl halide or alkyl sulfonate; or c) reductive amination of an aldehyde followed by reaction with an acylating agent such as an acyl chloride, a chloroformate, an isocyanate or a chlorocarbonyl amide or a sulfonylating agent such as a sulfonyl chloride, wherein one of the alkylating agents contains an appropriately protected carboxylic acid portion. Modification of the carboxylic acid portion to the appropriate ester, provides the desired compound of the invention. For example, reductive amination of 3-aminomethylphenoxy acetic acid isopropyl ester with 4-pyrazol-1-yl-benzaldehyde provides the secondary amine intermediate, 3-[4-pyrazol-1-yl-benzylamino)methyl]phenoxy acetic acid isopropyl ester, which undergoes amide formation with pyridine-3-sulfonyl chloride to provide the desired compound, 3-{[(4-pyrazol-1-yl-benzyl)-(pyridine-3-sulfonyl)-amino]methyl}phenoxy)-acetic acid isopropyl ester.

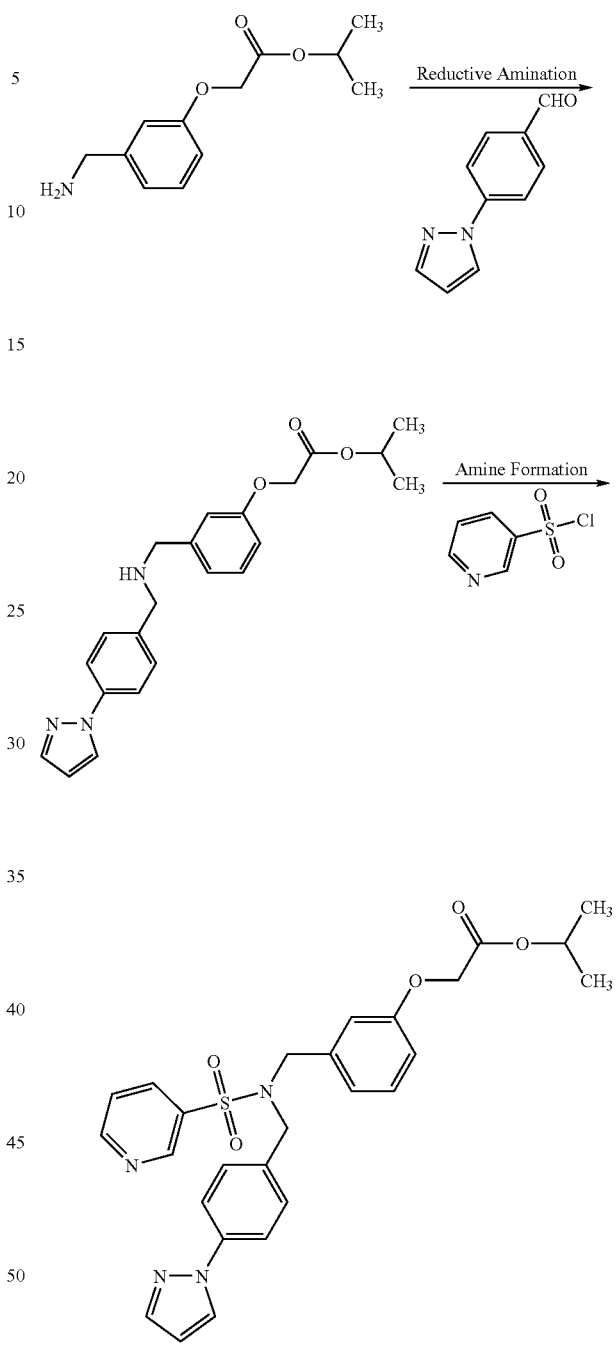

Alternatively, the compounds of the invention may be prepared through their corresponding carboxylic acid derivatives via an esterification route. As such, the carboxylic acid may first be deprotonated with a base, and then reacted with an electrophile to provide the corresponding ester. For example, deprotonation of 3-{[(4-pyrazol-1-yl-benzyl)-(pyridine-3-sulfonyl)amino]methyl}-phenoxy)acetic acid with potassium carbonate in the presence of a suitable solvent such as DMF, followed by treatment with isopropyl iodide, provides the desired compound, 3-{[(4-pyrazol-1-yl-benzyl)-(pyridine-3-sulfonyl)-amino]methyl}phenoxy)acetic acid isopropyl ester.

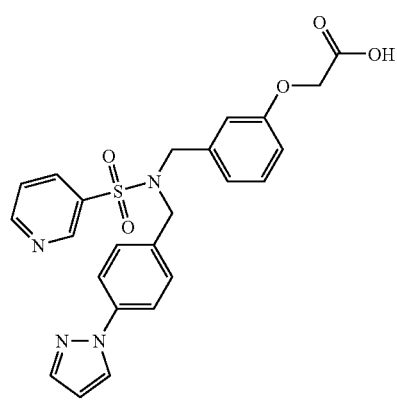

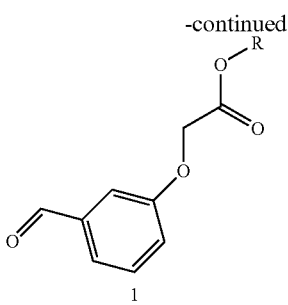

K₂CO₃, i-PrI, DMF →

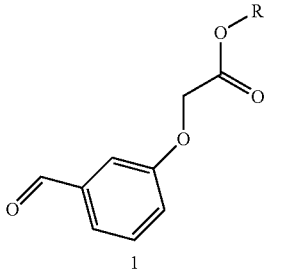

NH₂OH—HCl / MeOH, Pyr →

1

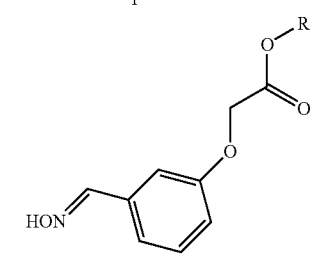

H₂, 1 atm 10% Pd/C / EtOH →

2

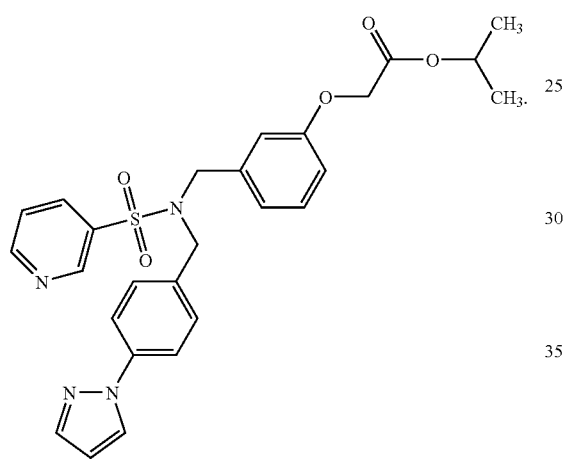

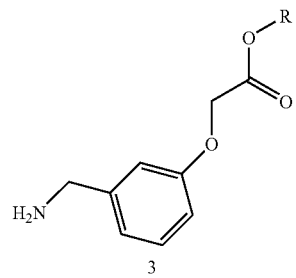

R'CHO / NaBH₄ or NaBH(OAc)₃ →

3

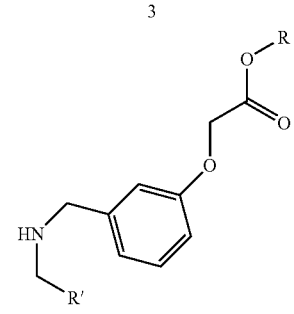

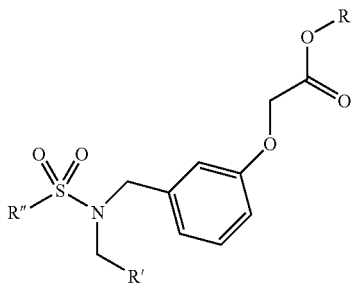

Et₃N, CH₂Cl₂ →

4

Still other methods include: a) O-alkylation of 3-hydroxybenzaldehyde with α-bromoacetic acid ester (R=Me, Et, i-Pr, t-Bu, etc.) using a base such as potassium tert-butoxide and solvent such as N,N-dimethylformamide to provide the O-alkylated product, 1; b) oxime formation of 1 with hydroxylamine hydrochloride in an alcoholic solvent such as methanol and base such as pyridine to provide 2; c) catalytic hydrogenation of 2 with a metal catalyst such as 10% palladium on carbon in the presence of H₂ and an alcoholic solvent such as ethanol to provide the amine 3; d) reductive amination of 3 with the appropriate aldehyde (R'CHO) and reducing agent such as sodium borohydride or sodium provides the amine 4; and e) N-alkylation of 4 with the appropriate sulfonyl chloride (R"SO₂Cl) in the presence of a base such as triethylamine and solvent such as dichloromethane provides the desired product 5.

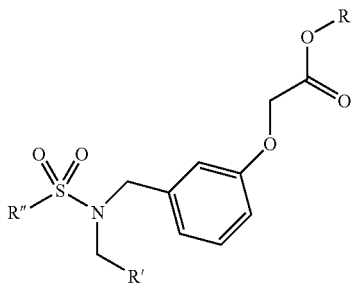

5

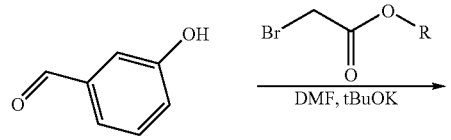

Other suitable reaction conditions are known to those of ordinary skill in the art and are exemplified in Protective Groups In Organic Synthesis, Second Edition, T. W. Greene and P. G. M. Wuts, John Wiley and Sons, Inc. 1991, pages 227-229, which is hereby incorporated by reference in its entirety for all purposes.

The utility of the compounds of the invention as medical agents for the reduction of intraocular pressure and accordingly to treat glaucoma is demonstrated by the activity of the compounds in conventional assays, including the in vivo assay and a receptor binding assay. Such assays also provide a means whereby the activities of the compounds can be compared to each other and with the activities of other known compounds. The results of these comparisons are useful for determining dosage levels in mammals, including humans, for the treatment of such diseases.

The compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis. The compounds of the invention may also be delivered to the front, side or back of the eye.

The compounds of the invention intended for pharmaceutical use may be administered alone or in combination with one or more other compounds of the invention or in combination with one or more other drugs (or as any combination thereof). There are several different classes of medications to treat glaucoma with several different medications in each class. Topical beta-adrenergic receptor antagonists such as timolol, levobunolol (Betagan), and betaxolol decrease aqueous humor production by the ciliary body. Alpha2-adrenergic agonists such as brimonidine (Alphagan) work by a dual mechanism, decreasing aqueous production and increasing uveo-scleral outflow. Less-selective sympathomimetics like epinephrine and dipivefin (Propine) increase outflow of aqueous humor through trabecular meshwork and possibly through uveoscleral outflow pathway, probably by a beta2-agonist action. Miotic agents (parasympathomimetics) like pilocarpine work by contraction of the ciliary muscle, tightening the trabecular meshwork and allowing increased outflow of aqueous through traditional pathways. Carbonic anhydrase inhibitors like dorzolamide (Trusopt), brinzolamide (Azopt), acetazolamide (Diamox) lower secretion of aqueous humor by inhibiting carbonic anhydrase in the ciliary body. Prostaglandin analogs like latanoprost (Xalatan), bimatoprost (Lumigan) and travoprost (Travatan) increase uveoscleral outflow of aqueous. Generally, such drugs and/or combinations thereof, will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).]

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Thus, compounds of the invention may be formulated as a solid, semi-solid, or thixotropic liquid for administration as an implanted depot providing modified release of the active compound. Examples of such formulations include drug-coated stents and PGLA [define] microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, J Pharm Sci, 88 (10), 955-958 by Finnin and Morgan (October 1999).]

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 μmg of the compound of the invention per actuation and the actuation volume may vary from 1 μl to 100 μl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff." The overall daily dose may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention may be administered in single or divided doses. Depending on the [disease and] condition of the patient, the term "treatment" as used herein may include one or more of curative, palliative and prophylactic treatment.

The ability of the compounds of the invention to reduce intraocular pressure may be measured using the assay described below.

EXAMPLES

The following non-limiting preparations and Examples illustrate the preparation of the compounds of the invention.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents: CDCl$_3$, deuterochloroform; D$_6$-DMSO, deuterodimethylsulphoxide; CD$_3$OD, deuteromethanol; THF, tetrahydrofuran. 'Ammonia' refers to a concentrated solution of ammonia in water possessing a specific gravity of 0.88. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Example 1
Preparation of isopropyl [3-({[4-(1H-pyrazol-1-yl)benzyl](pyridin-3-yl-sulfonyl)amino}methyl)phenoxy]acetate

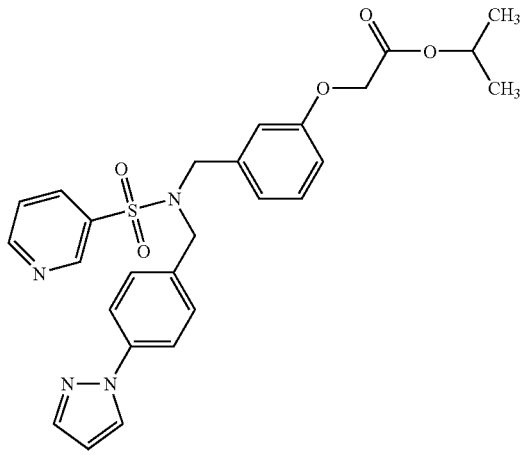

A. Preparation of (3-formyl phenoxy)acetic acid isopropyl ester

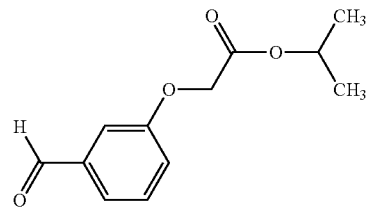

A solution of 3-hydroxybenzaldehyde (6.75 g, 55.2 mmol) in DMF (55 mL) was stirred at room temperature under a nitrogen atmosphere as potassium tert-butoxide (6.2 g, 55.3 mmol) was added in portions. The resulting suspension was stirred an additional 15 minutes at room temperature before isopropyl bromoacetate (7.10 mL, 55.2 mmol) was added. The reaction was stirred at room temperature for 15 h and was then quenched with water (250 mL). The resulting aqueous solution was extracted with ethyl acetate, and the combined organic layers were washed several times with water, dried over MgSO$_4$, filtered, and concentrated in vacuo. Purification via medium pressure liquid chromatography (0-10% hexane/ethyl acetate) afforded the title compound (5.2 g, 65%) as a clear oil. $^1$H NMR (400 MHz, CHLOROFORM-d) δ ppm 1.30 (d, 6H) 5.04-5.32 (m, 1H) 7.21-7.28 (m, 1H) 7.38 (s, 1H) 7.44-7.60 (m, 2H) 9.98 (s, 1H).

B. Preparation of [(3-hydroxyiminomethyl phenoxy)]acetic acid isopropyl ester

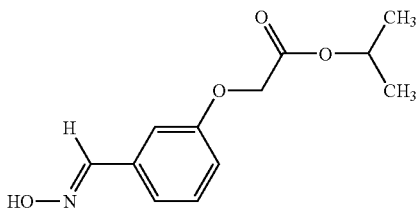

A solution of (3-formyl phenoxy)acetic acid isopropyl ester (3.7 g, 17 mmol) in methanol (55 mL) was stirred under nitrogen as hydroxylamine hydrochloride (1.2 g, 17 mmol) and pyridine (6 mL, 74 mmol) were added. The reaction was stirred for 15 h at room temperature. The volatiles were removed in vacuo and the residue was diluted with ethyl acetate. The resulting solution was washed with 1N HCl, and the resulting aqueous solution was washed with ethyl acetate. The combined organic layers were dried over MgSO$_4$, filtered, and concentrated in vacuo to give the title compound (4.13 g, 100%) as a pale yellow solid. $^1$H NMR (400 MHz, CHLOROFORM-d) δ ppm 1.36 (d, 6H) 4.67-4.72 (m, 2H) 5.15-5.34 (m, 1H) 7.01-7.07 (m, 1H) 7.33-7.36-7.43 (m, 2H) 8.17 (s, 1H). LRMS m/z calcd. for C$_{12}$H$_{15}$NO$_4$([M+H]$^+$): 237.1. Found: 238.1.

C. Preparation of [(3-aminomethyl phenoxy)]acetic acid isopropyl ester

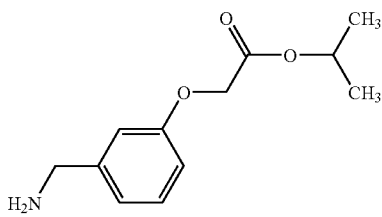

A suspension of [(3-hydroxyiminomethyl phenoxy)]acetic acid isopropyl ester (2.5 g, 11 mmol), 10% Pd/C (500 mg, 20 wt %), and conc. HCl (1 mL) in ethanol (150 mL) was hydrogenated at atmospheric pressure and room temperature for 7 hours. The suspension was filtered through a glass filter paper and the resulting yellow filtrate was concentrated in vacuo to afford the HCl salt of [(3-aminomethyl phenoxy)]acetic acid isopropyl ester (1.55 g, 60%) as a yellow solid. $^1$H NMR (400 MHz, MeOD) δ ppm 1.31 (d, 6H) 4.11 (s, 2H) 4.65-4.82 (m, 2H) 5.04-5.22 (m, 1H) 6.95-7.05 (m, 1H) 7.05-7.17 (m, 2H) 7.39 (t, J=7.96 Hz, 1H). LRMS m/z calcd. for $C_{12}H_{17}NO_3$ ([M+H]$^+$): 223.1 Found: 224.2.

D. Preparation of isopropyl [3-({[4-(1H-pyrazol-1-yl)benzyl]amino}methyl)-phenoxy]acetate

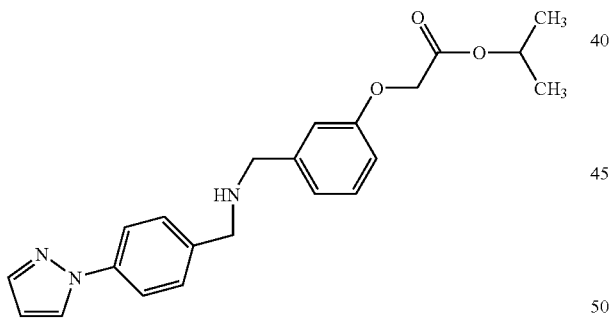

A solution of [(3-aminomethylphenoxy)]acetic acid isopropyl ester (0.40 g, 1.69 mmol), acetic acid (0.6 mL), and 4-pyrazoylbenzaldehyde (0.29 g, 1.69 mmol) in methanol (6 mL) was stirred at room temperature for 4 hours. After warming to 50° C. for 1 hour, the mixture was cooled to 0° C. and NaCNBH$_3$ (0.21 g, 3.31 mmol) was added. The mixture was allowed to warm to room temperature and stirred for 1 hour, followed by quenching with saturated aqueous Na$_2$CO$_3$. The aqueous mixture was extracted with ethyl acetate (3×75 mL), the organics were combined, dried over MgSO$_4$, filtered and concentrated in vacuo. The crude product was purified using medium pressure liquid chromatography (hexanes to 90% ethyl acetate/hexanes) to yield pure product (0.43 g, 65%) as a colorless oil. $^1$H NMR (400 MHz, CHLOROFORM-d) δ ppm 1.27 (d, J=6.32 Hz, 6H) 3.79 (s, 2H) 3.82 (s, 2H) 4.59 (s, 2H) 5.03-5.26 (m, 1H) 6.39-6.54 (m, 1H) 6.80 (dd, J=8.08, 2.53 Hz, 1H) 6.90-7.03 (m, 2H) 7.19-7.31 (m, 1H) 7.42 (d, J=8.34 Hz, 2H) 7.55-7.76 (m, 3H) 7.92 (d, J=2.27 Hz, 1H). LRMS m/z calcd. for $C_{22}H_{25}N_3O_3$ ([M+H]$^+$) 379.2. Found: 380.2.

E. Preparation of isopropyl [3-({[4-(1H-pyrazol-1-yl)benzyl](pyridin-3-ylsulfonyl)-amino}methyl)phenoxy]acetate

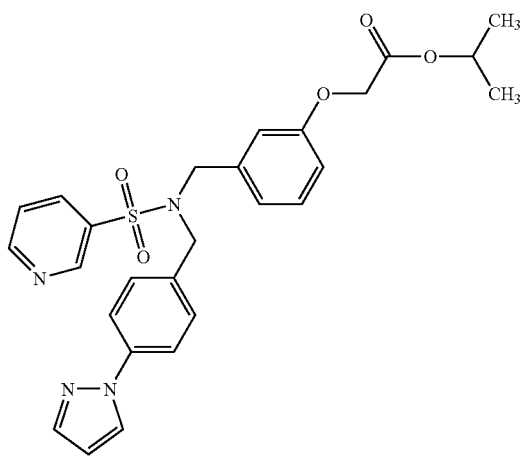

A solution of isopropyl [3-({[4-(1H-pyrazol-1-yl)benzyl]amino}methyl)-phenoxy]acetate (0.28 g, 0.75 mmol), triethylamine (0.53 mL, 0.37 mmol) and pyridine-3-sulfonyl chloride (268 mg, 1.50 mmol) in dichloromethane (7 mL) was stirred at room temperature for 15 hours. The mixture was diluted with dichloromethane, and the combined organic layers were washed with water, brine and dried over MgSO$_4$, filtered, and concentrated in vacuo. Purification by column chromatography (0-5% methanol in dichloromethane) afforded the desired product (180 mg, 69% based on the recovered amine starting material) as a pale yellow oil. $^1$H NMR (400 MHz, CHLOROFORM-d) δ ppm 1.29 (d, J=5.56 Hz, 6H) 4.37 (s, 2H) 4.42 (s, 2H) 4.50 (s, 2H) 5.06-5.25 (m, 1H) 6.49 (s, 1H) 6.65-6.75 (m, 2H) 6.77-6.84 (m, 1H) 7.17-7.23 (m, J=8.59 Hz, 3H) 7.46 (dd, J=7.83, 4.80 Hz, 1H) 7.60 (d, J=8.34 Hz, 2H) 7.74 (s, 1H) 7.92 (s, 1H) 8.08 (d, J=7.83 Hz, 1H) 8.83 (d, J=4.29 Hz, 1H) 9.09 (s, 1H). LRMS m/z calcd. for $C_{27}H_{28}N_4O_5S$ ([M+H]$^+$): 520.2. Found: 521.2.

The compounds listed in Table 1 were synthesized using the appropriate modifications of the above reagents and schemes:

TABLE 1

| Ex. No. | Example Compound | 1H NMR | LCMS (M + H) | EP2 cAMP EC50 (nM) | EP2 IC50 (nM) |
|---|---|---|---|---|---|
| 1 | 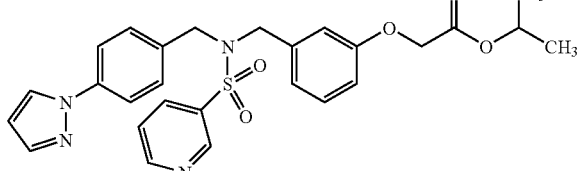<br>isopropyl [3-({[4-(1H-pyrazol-1-yl)-benzyl](pyridin-3-ylsulfonyl)amino}methyl)phenoxy]acetate | 1H NMR (400 MHz, CHLOROFORM-d) d ppm 1.29 (d, J=5.56 Hz, 6 H) 4.37 (s, 2 H) 4.42 (s, 2 H) 4.50 (s, 2 H) 5.06-5.25 (m, 1 H) 6.49 (s, 1 H) 6.65-6.75 (m, 2 H) 6.77-6.84 (m, 1H) 7.17-7.23 (m, J=8.59 Hz, 3 H) 7.46 (dd, J=7.83, 4.80 Hz, 1 H) 7.60 (d, J=8.34 Hz, 2 H) 7.74 (s, 1 H) 7.92 (s, 1 H) 8.08 (d, J=7.83 Hz, 1 H) 8.83 (d, J=4.29 Hz, 1 H) 9.09 (s, 1 H) | 521.2 | 1.48 | 10 |
| 2 | 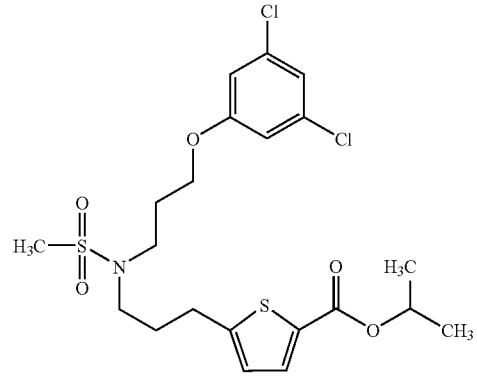<br>isopropyl 5-(3-{[3-(3,5-dichlorophenoxy)-propyl](methylsulfonyl)amino}-propyl)thiophene-2-carboxylate | 1H NMR (400 MHz, DICHLOROMETHANE-$d_2$) d ppm 1.27-1.36 (m, 6 H) 1.91-2.14 (m, 4 H) 2.81 (s, 3 H) 2.83-2.91 (m, 2 H) 3.17-3.26 (m, 2 H) 3.29-3.37 (m, 2 H) 4.00 (t, 2 H) 5.08-5.20 (m, 1 H) 6.77-6.84 (m, 3 H) 6.92-6.99 (m, 1 H) 7.57 (d, 1 H) | 509.3 | 8.15 | 3.22 |
| 3 | 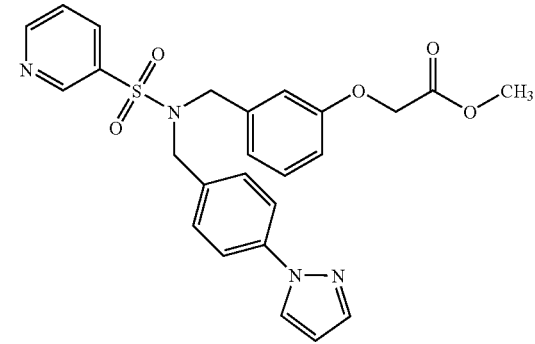<br>methyl [3-({[4-(1H-pyrazol-1-yl)benzyl](pyridin-3-ylsulfonyl)-amino}methyl)phenoxy]acetate | 1H NMR (400 MHz, DICHLOROMETHANE-$d_2$) d ppm 3.77 (s, 3 H) 4.30-4.43 (m, 4 H) 4.52 (s, 2 H) 6.41-6.50 (m, 1 H) 6.64 (d, 1 H) 6.69-6.80 (m, 2 H) 7.10-7.23 (m, 3 H) 7.46 (dd, 1 H) 7.53-7.63 (m, 2 H) 7.68 (d, 1 H) 7.94 (d, 1 H) 8.01-8.13 (m, 1 H) 8.80 (dd, 1 H) 9.04 (d, 1 H) | 493.3 | 1.48 | 10 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 4 | 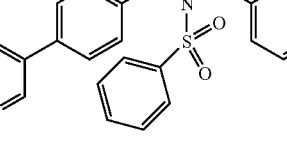<br>tert-butyl 3-(3-{[(phenylsulfonyl)(4-pyridin-3-ylbenzyl)amino]-methyl}-phenyl)propanoate | 1H NMR (400 MHz, DICHLOROMETHANE-d$_2$) d ppm 1.43 (s, 9 H) 2.35-2.49 (m, 2 H) 2.70-2.85 (m, 2 H) 4.37 (d, J=8.34 Hz, 4 H) 6.85 (s, 1 H) 6.91-6.97 (m, 1 H) 7.05-7.12 (m, 1 H) 7.17 (t, J=7.45 Hz, 1 H) 7.22 (d, J=8.08 Hz, 2 H) 7.36-7.43 (m, J=4.80 Hz, 1 H) 7.49 (d, J=8.34 Hz, 2 H) 7.57-7.64 (m, J=7.58, 7.58 Hz, 2 H) 7.65-7.72 (m, J=7.58 Hz, 1 H) 7.88-7.96 (m, 3 H) 8.60 (d, 1 H) 8.83 (s, 1 H) | 543.2 | 5.35 | <12.4 |
| 5 | 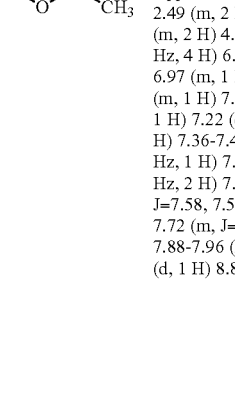<br>isopropyl 5-(3-{[2-(3,5-dichloro-phenoxy)ethyl](methylsulfonyl)amino}-propyl)thiophene-2-carboxylate | 1H NMR (400 MHz, DICHLOROMETHANE-d$_2$) d ppm 1.29-1.35 (m, 6 H) 1.97-2.09 (m, 2 H) 2.84-2.95 (m, 5 H) 3.25-3.35 (m, 2 H) 3.54-3.63 (m, 2 H) 4.05-4.14 (m, 2 H) 5.07-5.19 (m, 1 H) 6.76-6.86 (m, 3 H) 7.00 (t, 1 H) 7.59 (d, 1 H) | 495.4 | 4.8 | 4.42 |
| 6 | 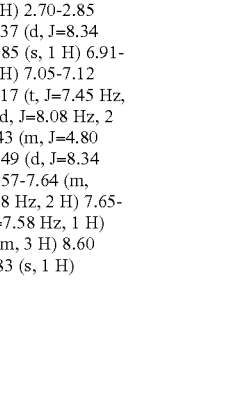<br>isopropyl 7-{[3-(3,5-dichloro-phenyl)propyl](methylsulfonyl)-amino}heptanoate | 1H NMR (400 MHz, DICHLOROMETHANE-d$_2$) d ppm 1.17-1.24 (m, 6 H) 1.27-1.39 (m, 4 H) 1.55-1.64 (m, 4H) 1.82-1.93 (m, 2H) 2.19-2.28 (m, 2 H) 2.56-2.66 (m, 2 H) 2.79 (s, 3 H) 3.08-3.20 (m, 4 H) 4.90-5.01 (m, 1 H) 7.13 (s, 2 H) 7.22 (s, 1 H) | 453.4 | 7 | 6.6 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 7 | 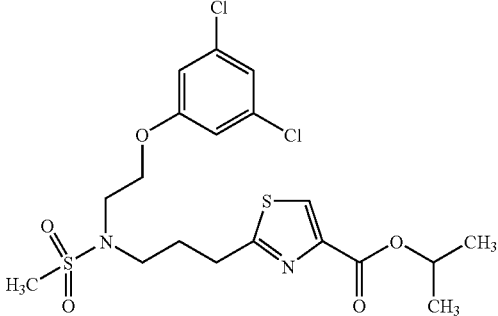 isopropyl 2-(3-{[2-(3,5-dichlorophenoxy)ethyl](methylsulfonyl)amino}propyl)-1,3-thiazole-4-carboxylate | 1H NMR (400 MHz, DICHLOROMETHANE-$d_2$) d ppm 1.34 (d, 6H) 2.12-2.25 (m, 2 H) 2.90 (s, 3 H) 3.09 (t, 2 H) 3.32-3.42 (m, 2 H) 3.57-3.66 (m, 2 H) 4.14 (t, 2 H) 5.14-5.26 (m, 1 H) 6.77-6.85 (m, 2 H) 6.98 (s, 1 H) 8.03 (s, 1 H) | 496.2 | 18 | 5.3 |
| 8 | 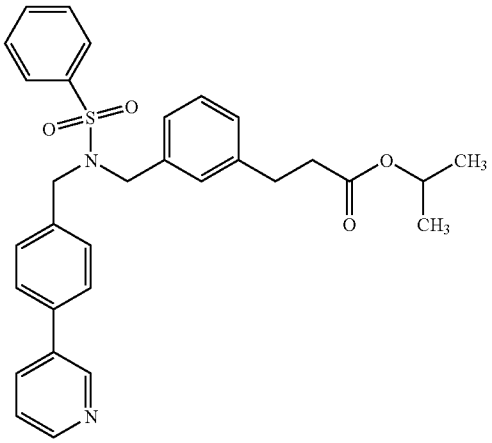 isopropyl 3-(3-{[(phenylsulfonyl)(4-pyridin-3-ylbenzyl)amino]-methyl}phenyl)propanoate | 1H NMR (400 MHz, DICHLOROMETHANE-$d_2$) d ppm 1.13-1.20 (m, 6 H) 2.35-2.48 (m, 2 H) 2.69-2.82 (m, 2 H) 4.34 (d, 4 H) 4.87-5.00 (m, 1 H) 6.81 (s, 1 H) 6.90 (d, 1 H) 7.00-7.24 (m, 4 H) 7.36 (dd, 1 H) 7.41-7.51 (m, 2 H) 7.52-7.69 (m, 3 H) 7.80-7.91 (m, 3 H) 8.55 (dd, 1 H) 8.79 (d, 1 H) | 529.4 | 5.35 | <12.4 |
| 9 | 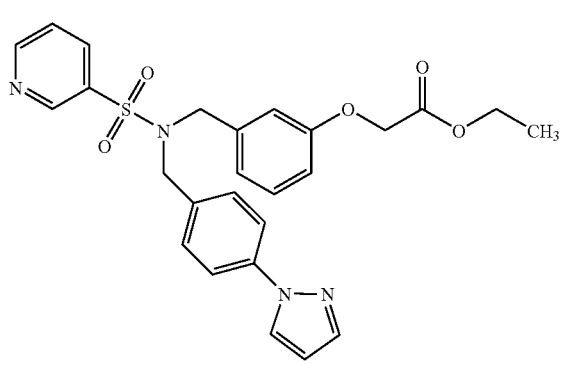 ethyl [3-({[4-(1H-pyrazol-1-yl)-benzyl](pyridin-3-ylsulfonyl)-amino}methyl)phenoxy]acetate | 1H NMR (400 MHz, DICHLOROMETHANE-$d_2$) d ppm 1.19-1.30 (m, 3 H) 4.18-4.26 (m, 2 H) 4.31-4.41 (m, 4 H) 4.47-4.52 (m, 2 H) 6.44-6.49 (m, 1 H) 6.61-6.66 (m, 1 H) 6.70-6.79 (m, 2 H) 7.13-7.21 (m, 3 H) 7.43-7.49 (m, 1 H) 7.54-7.61 (m, 2 H) 7.65-7.70 (m, 1 H) 7.90-7.95 (m, 1 H) 8.03-8.10 (m, 1 H) 8.76-8.83 (m, 1 H) 9.01-9.06 (m, 1 H) | 507.3 | 10 | 1.48 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 10 | tert-butyl 5-(3-{[3-(3,5-dichlorophenoxy)propyl](methylsulfonyl)amino}propyl)thiophene-2-carboxylate | 1H NMR (400 MHz, DICHLOROMETHANE-d$_2$) d ppm 1.45-1.52 (s, 9 H) 1.83-2.06 (m, 4 H) 2.75-2.86 (m, 6 H) 3.06-3.20 (m, 2 H) 3.21-3.31 (m, 2 H) 6.69-6.71 (m, J=3.79 Hz, 2 H) 6.74 (d, J=1.77 Hz, 2 H) 6.87-6.91 (m, J=1.77, 1.77 Hz, 1 H) 7.43 (d, J=3.79 Hz, 1 H) | 523.2 | 8.15 | 3.22 |
| 11 | tert-butyl 2-(3-{[2-(3,5-dichlorophenoxy)ethyl](methylsulfonyl)amino}propyl)-1,3-thiazole-4-carboxylate | 1H NMR (400 MHz, DICHLOROMETHANE-d$_2$) d ppm 1.40-1.53 (m, 9 H) 1.89-2.02 (m, 2 H) 2.73-2.88 (m, 5 H) 3.16-3.28 (m, 2 H) 3.50 (t, J=5.43 Hz, 2 H) 4.02 (t, J=5.31 Hz, 2 H) 6.67-6.74 (m, 2 H) 6.91 (t, J=1.64 Hz, 1 H) 7.45 (d, J=3.79 Hz, 1 H) | 510.2 | 18 | 5.3 |
| 12 | isopropyl [3-({[(1-methyl-1H-imidazol-4-yl)sulfonyl][4-(1,3-thiazol-2-yl)benzyl]amino}methyl)phenoxy]acetate | 1H NMR (400 MHz, DICHLOROMETHANE-d$_2$) d ppm 1.26 (d, 6 H) 3.71 (s, 3 H) 4.39 (d, 4 H) 4.50 (s, 2 H) 5.02-5.14 (m, 1 H) 6.71-6.82 (m, 3 H) 7.11-7.20 (m, 1 H) 7.26 (d, 2 H) 7.36 (d, 1 H) 7.42 (d, 1 H) 7.52 (d, 1 H) 7.79-7.87 (m, 3 H) | 541.1 | 12 | 26 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 13 | 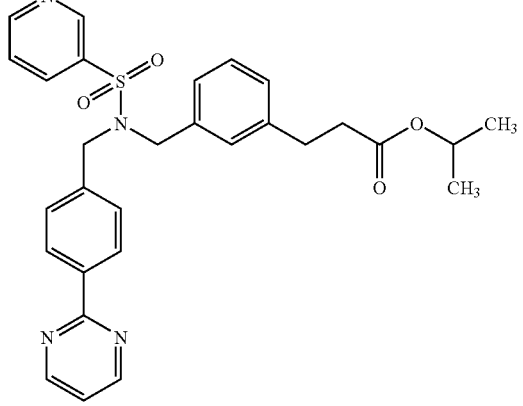 isopropyl 3-(3-{[(pyridin-3-ylsulfonyl)(4-pyrimidin-2-ylbenzyl)-amino]methyl}phenyl)propanoate | 1H NMR (400 MHz, DICHLOROMETHANE-$d_2$) d ppm 1.18 (d, 6 H) 2.41-2.51 (m, 2 H) 2.74-2.85 (m, 2 H) 4.40 (d, 4 H) 4.87-5.00 (m, 1 H) 6.86-6.99 (m, 2 H) 7.04-7.28 (m, 5 H) 7.44 (dd, 1 H) 8.02-8.11 (m, 1 H) 8.33 (d, 2 H) 8.75-8.83 (m, 3 H) 9.03 (d, 1 H) | 531.4 | 3.1 | <10.0 (n =2) |
| 14 | 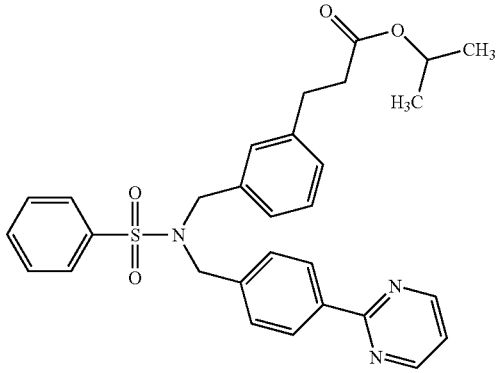 isopropyl 3-(3-{[(phenylsulfonyl)(4-pyrimidin-2-ylbenzyl)amino]-methyl)phenyl)propanoate | 1H NMR (400 MHz, DICHLOROMETHANE-$d_2$) d ppm 1.18 (d, 6 H) 2.36-2.48 (m, 2 H) 2.71-2.82 (m, 2 H) 4.35 (d, 4 H) 4.89-5.00 (m, 1 H) 6.77-6.85 (m, 1 H) 6.86-6.95 (m, 1 H) 7.01-7.09 (m, 1 H) 7.10-7.25 (m, 4 H) 7.51-7.69 (m, 3 H) 7.83-7.92 (m, 2 H) 8.25-8.35 (m, 2 H) 8.78 (d, 2 H) | 530.4 | 3.1 | <10.0 (n =2) |
| 15 | 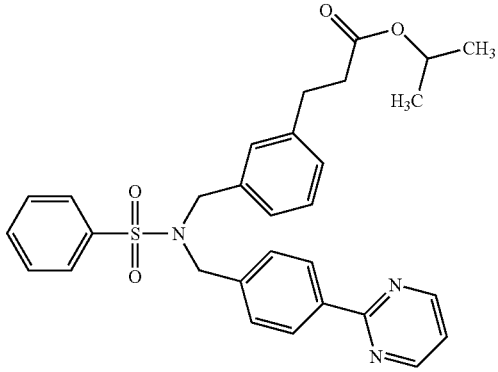 isopropyl 3-(3-{[(pyridin-2-ylsulfonyl)(4-pyrimidin-2-ylbenzyl)-amino]methyl}phenyl)propanoate | 1H NMR (400 MHz, DICHLOROMETHANE-$d_2$) d ppm 1.18 (d, 6 H) 2.38-2.51 (m, 2 H) 2.71-2.84 (m, 2 H) 4.50 (d, 4 H) 4.87-5.00 (m, 1 H) 6.91 (s, 1 H) 6.93-6.99 (m, 1 H) 7.01-7.07 (m, 1 H) 7.10-7.16 (m, 1 H) 7.17-7.26 (m, 3 H) 7.44-7.55 (m, 1 H) 7.85-8.01 (m, 2 H) 8.29 (d, 2 H) 8.68 (s, 1 H) 8.78 (d, 2 H) | 531.4 | 4.9 | <10.0 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 16 | 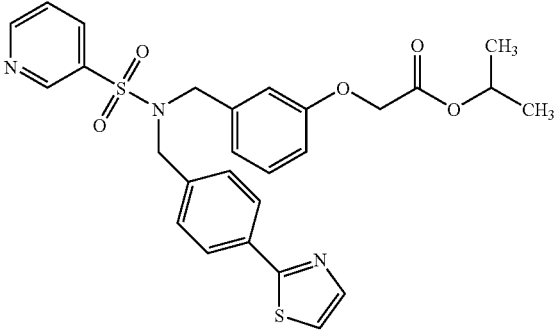 isopropyl [3-({(pyridin-3-ylsulfonyl)-[4-(1,3-thiazol-2-yl)-benzyl]-amino}methyl)phenoxy]acetate | 1H NMR (400 MHz, DICHLOROMETHANE-d$_2$) d ppm 1.21-1.30 (m, 6 H) 4.31-4.51 (m, 6 H) 5.03-5.15 (m, 1 H) 6.65 (s, 1 H) 6.75 (dd, 2 H) 7.11-7.21 (m, 3 H) 7.37 (d, 1 H) 7.46 (dd, 1 H) 7.78-7.88 (m, 3 H) 8.02-8.10 (m, 1 H) 8.79 (dd, 1 H) 9.03 (d, 1 H) | 538.4 | 0.85 | 3 |
| 17 | 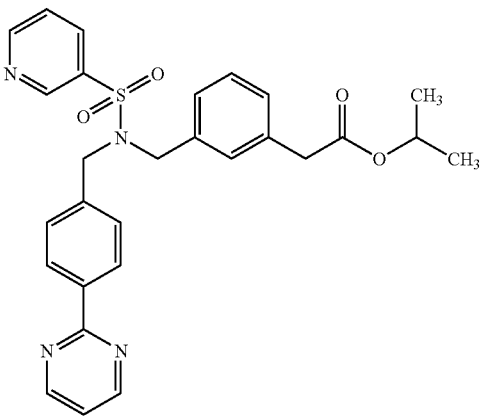 isopropyl (3-{[[(pyridin-3-ylsulfonyl)-(4-pyrimidin-2-ylbenzyl)amiuno]-methyl}phenyl)acetate | 1H NMR (400 MHz, DICHLOROMETHANE-d$_2$) d ppm 1.21 (d, 6 H) 3.47 (s, 2 H) 4.41 (d, 4 H) 4.92-5.02 (m, 1 H) 6.97-7.06 (m, 2 H) 7.11-7.28 (m, 5 H) 7.38-7.50 (m, 1 H) 8.00-8.09 (m, 1 H) 8.32 (d, 2 H) 8.79 (d, 3 H) 9.03 (d, 1 H) | 517.2 | 7.8 | 3.9 |
| 18 | 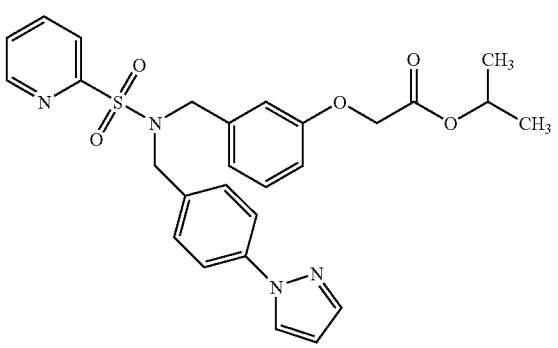 isopropyl [3-({[4-(1H-pyrazol-1-yl)benzyl](pyridin-2-ylsulfonyl)-amino}methyl)phenoxy]acetate | 1H NMR (400 MHz, DICHLOROMETHANE-d$_2$) d ppm 1.22-1.30 (m, 6 H) 4.42-4.55 (m, 6 H) 5.01-5.17 (m, 1 H) 6.40-6.50 (m, 1 H) 6.65-6.82 (m, 3 H) 7.08-7.24 (m, 3 H) 7.45-7.59 (m, 3 H) 7.67 (s, 1 H) 7.86-8.02 (m, 3 H) 8.69 (d, 1 H). | 521.4 | 12 | <10 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 19 | 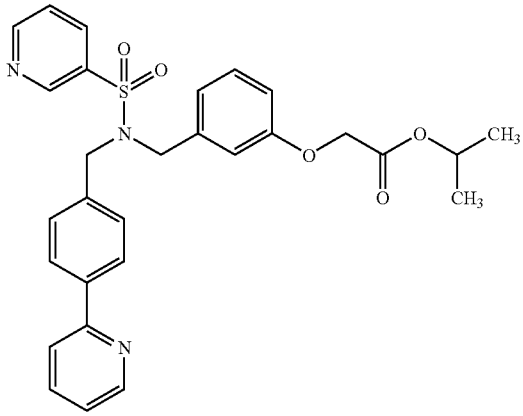<br>isopropyl (3-{[(4-pyridin-2-ylbenzyl)(pyridin-3-ylsulfonyl)-amino]methyl}phenoxy)acetate | 1H NMR (400 MHz, DICHLOROMETHANE-d$_2$) d ppm 1.22-1.29 (m, 6 H) 4.32-4.51 (m, 6 H) 5.03-5.15 (m, 1 H) 6.62-6.68 (m, 1 H) 6.72-6.80 (m, 2 H) 7.11-7.29 (m, 4 H) 7.45 (dd, 1 H) 7.68-7.79 (m, 2 H) 7.86-7.92 (m, 2 H) 8.02-8.10 (m, 1 H) 8.65 (dd, 1 H) 8.79 (dd, 1 H) 9.03 (d, 1 H) | 532.4 | 4.1 | 7.6 |
| 20 | 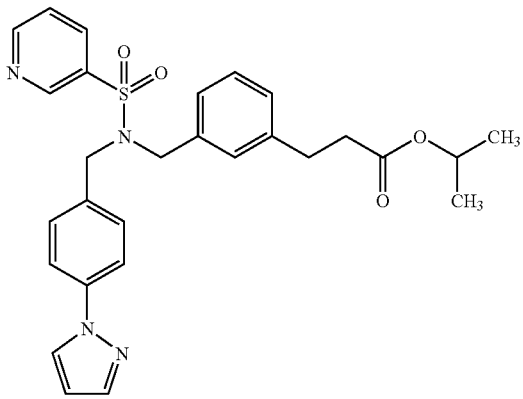<br>isopropyl 3-[3-({[4-(1H-pyrazol-1-yl)benzyl](pyridin-3-ylsulfonyl)-amino}methyl)phenyl]propanoate | 1H NMR (400 MHz, DICHLOROMETHANE-d$_2$) d ppm 1.15-1.20 (m, 6 H) 2.40-2.50 (m, 2 H) 2.80 (t, 2 H) 4.36 (d, 4 H) 4.89-4.99 (m, 1 H) 6.43-6.51 (m, 1 H) 6.85-6.97 (m, 2 H) 7.04-7.11 (m, 1 H) 7.11-7.22 (m, 3 H) 7.40-7.49 (m, 1 H) 7.53-7.62 (m, 2 H) 7.68 (d, 1 H) 7.94 (d, 1 H) 8.01-8.10 (m, 1 H) 8.80 (dd, 1 H) 9.03 (d, 1 H). | 519.4 | 51.5 | <10.0 |
| 21 | 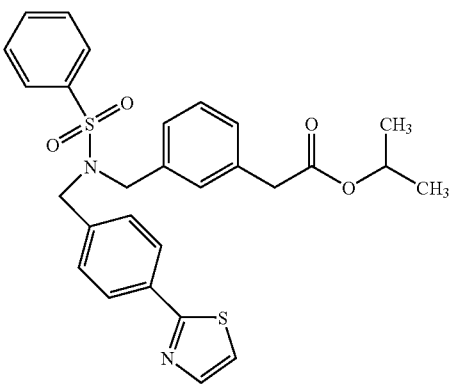<br>isopropyl [3-({(pyridin-3-ylsulfonyl)-[4-(1,3-thiazol-2-yl)benzyl]amino}-methyl)phenyl]acetate | 1H NMR (400 MHz, DICHLOROMETHANE-d$_2$) d ppm 1.17-1.24 (m, 6 H) 3.47 (s, 2 H) 4.39 (d, 4 H) 4.90-5.03 (m, 1 H) 6.95-7.03 (m, 2 H) 7.10-7.23 (m, 4 H) 7.37 (d, 1 H) 7.44 (dd, 1 H) 7.79-7.87 (m, 3 H) 8.01-8.08 (m, 1 H) 8.79 (dd, 1 H) 9.03 (d, 1 H). | 522.3 | 2.2 | 2.2 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 22 | 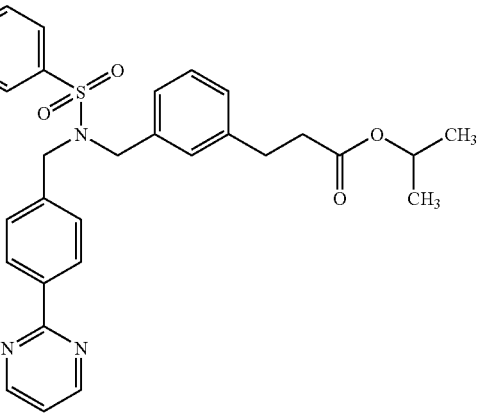<br>isopropyl 3-[3-({[(4-chlorophenyl)-sulfonyl](4-pyrimidin-2-ylbenzyl)-amino}methyl)phenyl]propanoate | 1H NMR (400 MHz, DICHLOROMETHANE-$d_2$) d ppm 1.13-1.20 (m, 6 H) 2.45 (t, 2 H) 2.79 (t, 2 H) 4.35 (d, 4 H) 4.87-5.00 (m, 1 H) 6.85 (s, 1 H) 6.93 (d, 1 H) 7.07 (d, 1 H) 7.12-7.24 (m, 4 H) 7.52 (d, 2 H) 7.79 (d, 2 H) 8.32 (d, 2 H) 8.79 (d, 2 H). | 565.1 | 3.3 | 15.7 |
| 23 | 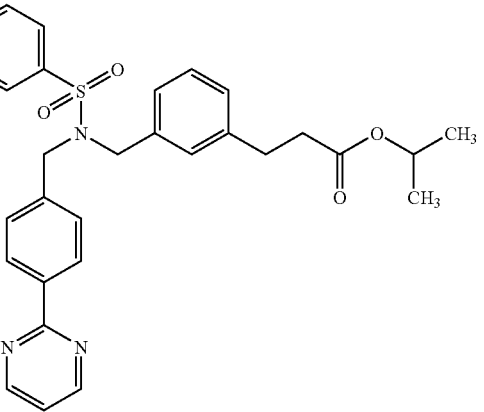<br>isopropyl (3-{[(pyridin-3-ylsulfonyl)-(4-pyrimidin-2-ylbenzyl)amino]-methyl}phenoxy)acetate | 1H NMR (400 MHz, DICHLOROMETHANE-$d_2$) d ppm 1.21-1.29 (m, 6 H) 4.37 (s, 2 H) 4.40-4.50 (m, 4 H) 5.04-5.13 (m, 1 H) 6.62-6.68 (m, 1 H) 6.71-6.80 (m, 2 H) 7.12-7.25 (m, 4 H) 7.45 (dd, 1 H) 8.02-8.10 (m, 1 H) 8.27-8.36 (m, 2 H) 8.73-8.83 (m, 3 H) 9.03 (d, 1 H). | 533.4 | 5.4 | 22 |
| 24 | 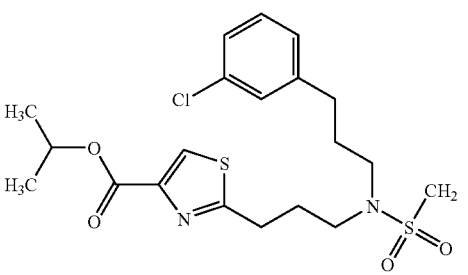<br>isopropyl 2-(3-{[3-(3-chlorophenyl)-propyl](methylsulfonyl)amino)-propyl)-1,3-thiazole-4-carboxylate | 1H NMR (400 MHz, DICHLOROMETHANE-$d_2$) d ppm 1.31-1.37 (m, , 6 H) 1.84-1.95 (m, 2 H) 2.05-2.16 (m, 2 H) 2.58-2.66 (m, 2 H) 2.81 (s, 3 H) 3.07 (t, 2 H) 3.15-3.32 (m, 4 H) 5.15-5.25 (m, 1 H) 7.06-7.28 (m, 4 H) 8.03 (s, 1 H) | 460.2 | 54 | 6.64 |

TABLE 1-continued

| Ex. No. | Example Compound | 1H NMR | LCMS (M + H) | EP2 cAMP EC50 (nM) | EP2 IC50 (nM) |
|---|---|---|---|---|---|
| 25 | 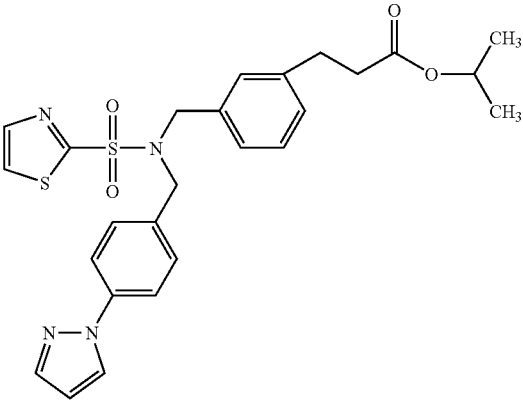<br>isopropyl 3-[3-({[4-(1H-pyrazol-1-yl)benzyl](1,3-thiazol-2-ylsulfonyl)-amino}methyl)phenyl]propanoate | 1H NMR (400 MHz, DICHLOROMETHANE-$d_2$) d ppm 1.22 (d, J=6.32 Hz, 6 H) 2.51 (t, J=7.83 Hz, 2 H) 2.85 (t, J=7.83 Hz, 2 H) 4.51 (s, 2 H) 4.53 (s, 2 H) 4.90-5.09 (m, 1 H) 6.51 (s, 1 H) 6.96-7.04 (m, 2 H) 7.09-7.15 (m, 1 H) 7.17-7.31 (m, 3 H) 7.61 (d, J=8.34 Hz, 2 H) 7.68-7.76 (m, 2 H) 7.95-8.00 (m, 1 H) 8.03 (d, J=3.03 Hz, 1 H) | 525.2 | 5.9 | <10 |
| 26 | 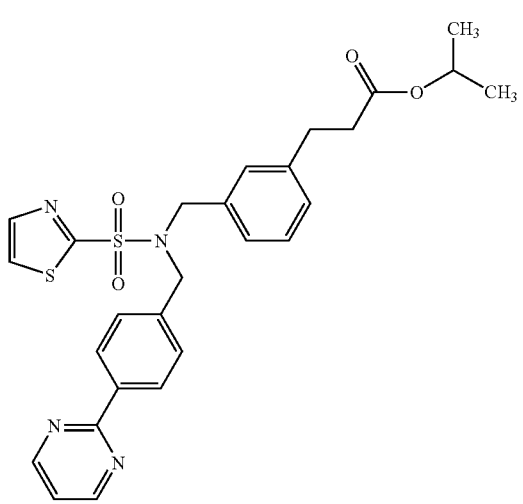<br>isopropyl 3-(3-{[(4-pyrimidin-2-ylbenzyl)(1,3-thiazol-2-ylsulfonyl)-amino]methyl}phenyl)propanoate | 1H NMR (400 MHz, DICHLOROMETHANE-$d_2$) d ppm 1.10 (d, J=6.32 Hz, 6 H) 2.39 (t, 2 H) 2.73 (t, J=7.83 Hz, 2 H) 4.41 (s, 2 H) 4.46 (s, 2 H) 4.81-4.94 (m, 1 H) 6.83-6.93 (m, 2 H) 6.96-7.04 (m, 1 H) 7.05-7.23 (m, 4 H) 7.58 (d, J=3.28 Hz, 1 H) 7.91 (d, J=3.03 Hz, 1 H) 8.24 (d, J=8.34 Hz, 2 H) 8.71 (d, J=4.80 Hz, 2 H) | 537.2 | 6.4 | <10 |
| C12* | 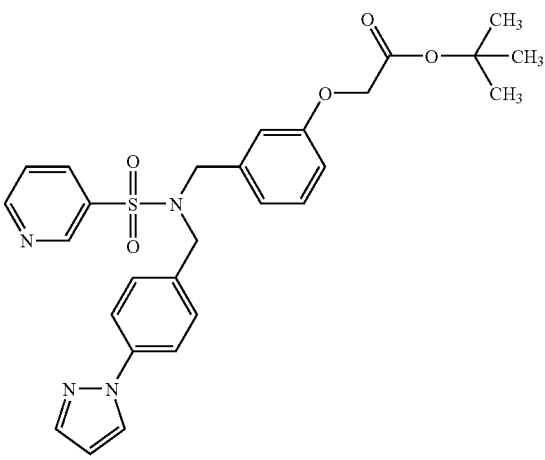 | See US2003/0078261 | NA | 1.48 | 10 |

*Comparative compound 12 ('C12') is from US Publication No. 2003/0078261.

Assay for Binding to Prostaglandin E2 Receptors

Membrane Preparation

All operations are performed at 4° C. Transfected cells expressing prostaglandin E2 type 1 receptors (EP1), type 2 (EP2), type 3 (EP3) or type 4 (EP4) receptors are harvested and suspended to 2 million cells per ml in Buffer A [50 mM Tris-HCl (pH 7.4), 10 mM $MgCl_2$, 1 mM EDTA, 1 mM Pefabloc peptide, (Sigma, St. Louis, Mo.), 10 uM Phosporamidon peptide, (Sigma, St. Louis, Mo.), 1 uM Pepstatin A peptide, (Sigma, St. Louis, Mo.), 10 uM Elastatinal peptide, (Sigma, St. Louis, Mo.), 100 uM Antipain peptide, (Sigma, St. Louis, Mo.)]. These are lysed by sonification with a Branson Sonifier (Model #250, Branson Ultrasonics Corporation, Danbury, Conn.) in 2 fifteen second bursts. Unlysed cells and debris are removed by centrifugation at 100.times.g for 10 min. Membranes are then harvested by centrifugation at 45,000.times.g for 30 minutes. Pelleted membranes are resuspended to 3-10 mg protein per ml, protein concentration being determined according to the method of Bradford [Bradford, M., Anal. Biochem., 72, 248 (1976)]. Resuspended membranes are then stored frozen at −80° C. until use.

Binding Assay

Frozen membranes as prepared are thawed and diluted to 1 mg protein per ml in Buffer A. One volume of membrane preparation is combined with 0.05 volume test compound or buffer and one volume of 3 nM 3H-prostaglandin E2 (#TRK 431, Amersham, Arlington Heights, Ill.) in Buffer A. The mixture (205 μL total volume) is incubated for 1 hour at 25° C. The membranes are then recovered by filtration through type GF/C glass fiber filters (#1 205401, Wallac, Gaithersburg, Md.) using a Tomtec harvester (Model Mach II/96, Tomtec, Orange, Conn.). The membranes with bound 3H-prostaglandin E2 are trapped by the filter, the buffer and unbound 3H-prostaglandin E2 pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of 3H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound 3H-prostaglandin E2.

Example 3

(+/−)-15-Deoxy-16S-hydroxy-17-cyclobutyl PGE1; (+/−)-15-deoxy 16S-hydroxy-17-cyclobutyl prostaglandin E1 (Butaprost)

Butaprost, a structural analog of PGE2, is a selective agonist for the EP2 receptor subtype. EP2 receptors are expressed on human neutrophils and on respiratory, vascular and uterine smooth muscle. Butaprost binds with about 1/10 the affinity of PGE2 to the recombinant murine EP2 receptor, and does not bind appreciably to any of the other murine EP receptors or DP, TP, FP or IP receptors. The EC50 for the stimulation of cAMP by butaprost in COS cells transfected with the human EP2 receptor is about 5 μM, while the EC50 for PGE2 in this assay is about 43 nM. Butaprost has frequently been used to pharmacologically define the EP receptor expression profile of various human and animal tissues and cells.

Tables 2 and 3 describe the intraocular pressure (IOP) changes that were seen following topical application of EP2 agonists in ocular hypertensive non-human primates. Typically, compounds in suitable formulations were dosed topically and IOP was measured using tonometry. Changes in IOP between vehicle treatment followed by treatment with EP2 compounds were assessed over time in the dosed hypertensive eye. ΔΔ Emax reflects the difference in IOP from EP2 compound-treated eye over that seen for vehicle-treated eye at the timepoint wherein maximum IOP reduction for compound was seen. The percent ΔΔ Emax was the percentage change in IOP reduction conferred by compound over that for vehicle (set at 100%). Tmax represents the time point at which maximum IOP reduction of compound was observed. The data provided here showed statistical significance. NS represents not significant. Table 2 compares acids of EP2 compound while Table 3 compares IOP response seen with esters of certain acids. Esters provide better corneal penetration and improved drug exposure in the anterior chamber compared to acids and are therefore dosed at 1/5th the dose for acids (0.1 mg/ml).

TABLE 2

Primate IOP Summary of acid EP2 Agonists

| Comparative Compound | Conc (%) | BL (mmHg) | ΔΔEmax (mm Hg) | ΔΔEmax (%) | Tmax (h) |
|---|---|---|---|---|---|
| Butaprost C1 | 0.1 | 37 | −5.5 | −18 | 5 |
| C2 | 0.1 | 36 | −4.4 | −11 | 2 |

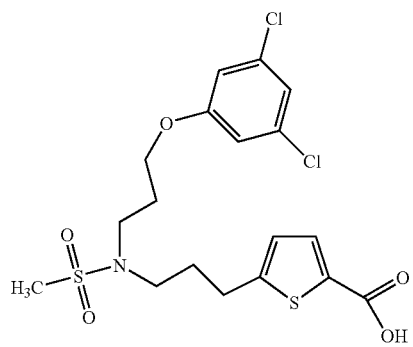

TABLE 2-continued
Primate IOP Summary of acid EP2 Agonists
| Comparative Compound | Conc (%) | BL (mmHg) | ΔΔEmax (mm Hg) | ΔΔEmax (%) | Tmax (h) |
|---|---|---|---|---|---|
| 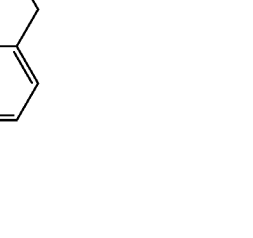 C3/(C11) | 0.1 | 35 | −7.0 | −21 | 4 |
| 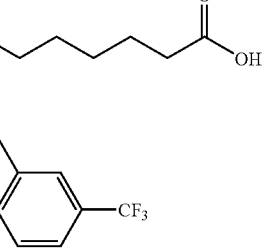 C4 | 0.1 | 32 | −3.7 | −9 | 6 |
| 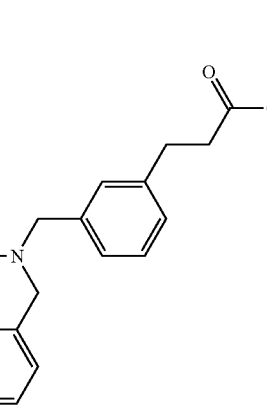 C5 | 0.1 | 28 | ns | ns | — |

TABLE 2-continued
Primate IOP Summary of acid EP2 Agonists
| Comparative Compound | Conc (%) | BL (mmHg) | ΔΔEmax (mm Hg) | ΔΔEmax (%) | Tmax (h) |
|---|---|---|---|---|---|
| 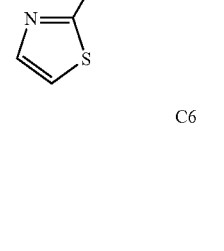 C6 | 0.1 | 32 | ns | ns | — |
| 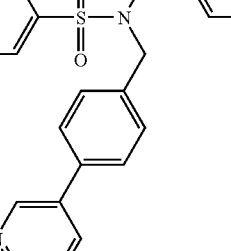 C7 | 0.1 | 31 | ns | ns | — |
| 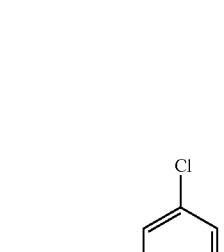 C8 | 0.1 | 34 | −4.3 | −8 | 2 |

TABLE 2-continued
Primate IOP Summary of acid EP2 Agonists
| Comparative Compound | Conc (%) | BL (mmHg) | ΔΔEmax (mm Hg) | ΔΔEmax (%) | Tmax (h) |
|---|---|---|---|---|---|
| 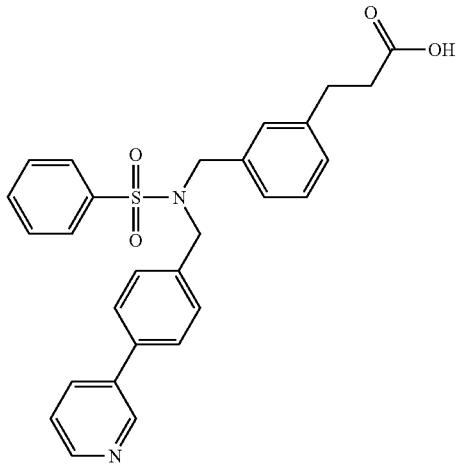 C9 | 0.1 | 33 | −3.0 | −10 | 4 |
| 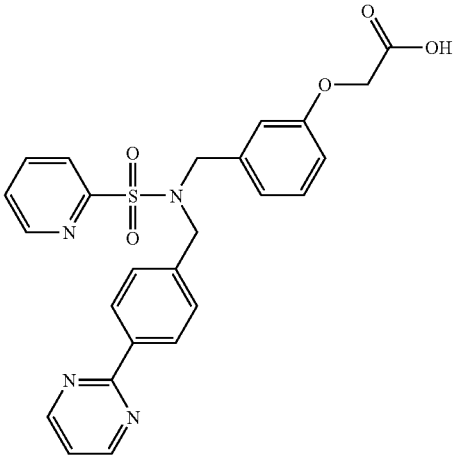 C10 | 0.1 | 36 | ns | ns | — |

TABLE 2-continued
Primate IOP Summary of acid EP2 Agonists
| Comparative Compound | Conc (%) | BL (mmHg) | ΔΔEmax (mm Hg) | ΔΔEmax (%) | Tmax (h) |
| --- | --- | --- | --- | --- | --- |
| C11/(C3) | 0.1 | 46 | −2.6 | −6 | 4 |
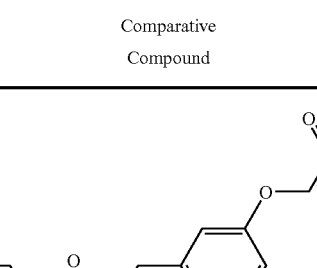
TABLE 3
Isopropylesters Tested in OHT Primates
| Compound | BL (mmHg) | ΔΔEmax (mmHg) | ΔΔEmax (%) | Tmax (h) |
| --- | --- | --- | --- | --- |
| 1 | 42 | −14 (OHT) −7.5 (NT) | −47 −31 | 6 |

TABLE 3-continued

Isopropylesters Tested in OHT Primates

| Compound | BL (mmHg) | ΔΔEmax (mmHg) | ΔΔEmax (%) | Tmax (h) |
|---|---|---|---|---|
| 2 | 36 | ns | ns | ns |
| 7 | 36 | −8 (both eyes) | 24 | 4-6 |

Example 4

Comparison of Efficacy (Change in Intraocular Pressure) Between Isopropyl Ester (Example 1) and Tert-Butyl Ester (Comparative Compound 12 "C12", US2003/0078261) as Assessed in Glaucomatous Dogs Typically, compounds in suitable formulations were dosed topically and IOP was measured using tonometry. A single 50 μl drop containing either vehicle or drug was instilled in each eye of glaucomatous dogs and IOP was measured at 1, 2, 4, and 6 hours post dose. A baseline IOP measurement was taken prior to topical instillation of vehicle or drug. Changes in IOP between vehicle treatment followed by treatment with EP2 compounds were assessed over time in the glaucomatous dogs. ΔΔ Emax reflects the difference in IOP±standard error from EP2 compound-treated eye over that seen for vehicle-treated eye at the time point wherein maximum IOP reduction for compound was seen. The percent ΔΔ Emax was the percentage change in IOP reduction conferred by compound over that for vehicle (set at 100%).

It is to be noted that even though the maximum IOP reduction between C12 and Example 1 appeared to be similar i.e. between 7-8 mmHg (33-34%), C12 was dosed at 4 times higher concentration than Example 1.

TABLE 4
| Compound No. | Concentration | ΔΔEmax (mmHg) | ΔΔEmax % |
| --- | --- | --- | --- |
| 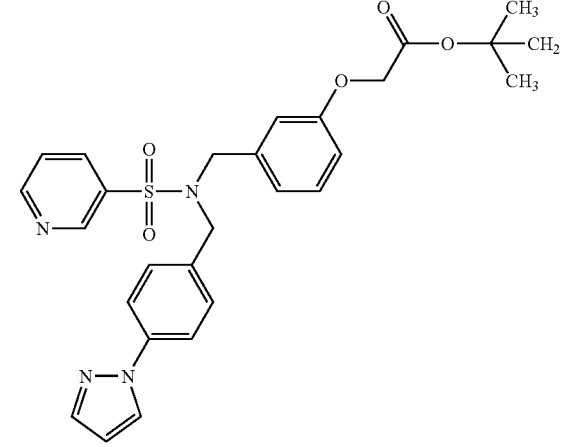<br>Comparative Compound 12<br>(C12) | 0.43 mg/ml<br>(0.043%) | −8.0 1.7 ± mmHg @ 6 h | −34% @ 6 h |
| 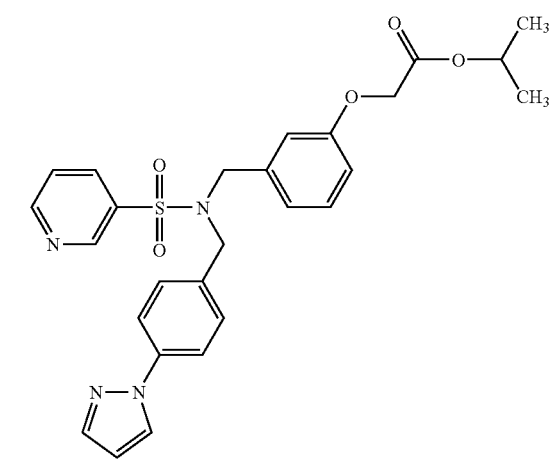<br>Example 1 | 0.1 mg/ml<br>(0.01%) | −7.0 1.2 ± mmHg @ 6 h | −33% @ 6 h |

Example 5

Powder X-Ray Diffraction Patterns of Isopropyl Versus T-Butyl Compounds

FIG. 1 shows the powder X-ray diffraction pattern of both C12 (t-butyl ester) and Example 1 (isopropyl ester).

The powder X-ray diffraction patterns were collected using a Bruker AXS D8-Discover diffractometer equipped with Cu K a radiation 1.54 A X-ray radiation source operated at 40 kV and 40 mA. During analysis, the samples were analyzed from angles of 4 to 40 degrees (θ-2θ) using a scan time of 60 seconds and a scan spot size of 0.5 mm.

The X-Ray diffraction peaks, characterized by peak positions and intensity assignments, have been extracted from the X-ray powder diffractogram of Example 1 and comparative compound 12. One of skill in the art will appreciate that the peak positions (2θ) will show some inter-apparatus variability, typically as much as 0.1 degrees. Accordingly, where peak positions (2θ) are reported, one of skill in the art will recognize that such numbers are intended to encompass such inter-apparatus variability.

As seen in FIG. 1, Example 1 manifests as a crystalline form with characteristic peaks at diffraction angles (2θ) of 8.6±0.1, 13.5±0.1, 17.6±0.1, 19.2±0.1, and 21.9±0.1, whereas C12 form and has no characteristic peaks. Example 1 yielded a solid active ingredient that was relatively easier to formulate into a drug product, whereas C12 yielded a gummy material that was difficult to handle.

What is claimed is:

1. A compound of the formula:

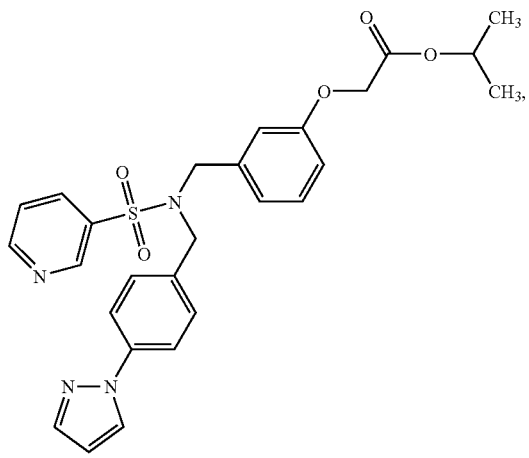

or a pharmaceutically acceptable salt thereof.

2. A pharmaceutical composition, comprising a compound of claim 1, or a pharmaceutically acceptable salt thereof, and a pharmaceutically acceptable excipient.

3. A method for reducing intraocular pressure in a mammal comprising administering to said mammal a therapeutically effective amount of a compound of the formula:

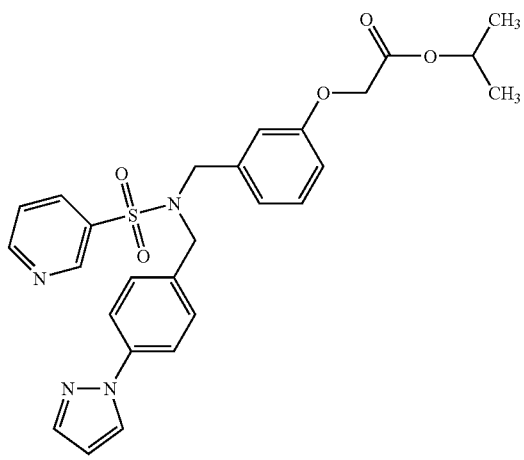

or a pharmaceutically acceptable salt thereof.

4. The method of claim 3, wherein said intraocular pressure is treated in a human.

5. The method of claim 3, wherein about 0.00001 mg/day to about 10 mg/day of the compound is administered.

6. The method of claim 3, wherein the compound is administered topically.

7. The method of claim 3, wherein said intraocular pressure is reduced in treating glaucoma.

* * * * *